US006967240B1

(12) United States Patent
Dietrich et al.

(10) Patent No.: US 6,967,240 B1
(45) Date of Patent: Nov. 22, 2005

(54) CONGENER INDEPENDENT DETECTION OF MICROCYSTIN AND NODULARIN CONGENERS

(75) Inventors: Daniel R. Dietrich, Unterdorf, CH-8566 Neuwilen (CH); Werner Fischer, Epalinges (CH); A. Richard Chamberlin, Irvine, CA (US); James B. Aggen, San Francisco, CA (US); Ian Garthwaite, Hamilton (NZ); Christopher O. Miles, Oslo (NO); Kathryn M. Ross, Hamilton (NZ); Neale R. Towers, Hamilton (NZ)

(73) Assignees: Daniel R. Dietrich, Neuwilen (CH); The Regent of the University of California, Oakland, CA (US); New Zealand Agricultural Research Institute Limited, Hamilton (NZ)

( * ) Notice: Subject to any disclaimer, the term of this patent is extended or adjusted under 35 U.S.C. 154(b) by 0 days.

(21) Appl. No.: 10/070,302

(22) PCT Filed: Sep. 6, 2000

(86) PCT No.: PCT/EP00/08711

§ 371 (c)(1),
(2), (4) Date: May 1, 2002

(87) PCT Pub. No.: WO01/18059

PCT Pub. Date: Mar. 15, 2001

(30) Foreign Application Priority Data

Sep. 6, 2000 (EP) .................................. 99116881

(51) Int. Cl.[7] ....................... C07K 16/12; C07K 17/08; G01N 30/01; G01N 33/545

(52) U.S. Cl. ................. 530/389.5; 435/7.93; 435/7.95; 435/188; 436/161; 436/531; 530/388.9; 530/389.8; 530/391.1; 530/388.4; 530/403; 530/405; 530/406

(58) Field of Search ................................ 436/531, 815, 436/161; 435/7.93, 7.95, 188; 530/389.8, 530/388.9, 403, 405, 406, 389.5, 388.4, 391.1

(56) References Cited

OTHER PUBLICATIONS

J. An et al, Toxicon 32(12): 1495-1507 (1994). Use of a colorimetric protein phosphatase inhibition assay and ELISA for the study of Microcystins and Nodularins.*

X. Huang et al.: "Production and characterization of monoclonal antibodies against the blue-green algal toxin microcystin." Abstracts of the General Meeting of the American Society For Microbiology, vol. 96, 1996, p. 380 XP000982157, USA. Abstract P-64.

S. Nagata et al.: "Novel monoclonal antibodies against microcystin and their protective activity for hepatotoxicity." Natural Toxins, vol. 3, No. 2, 1995, pp. 78-86, XP000982191, New York, NY, USA.

S. Nagata et al.: "Enzyme immunoassay for direct determination of microcystins in enviromental water." Journal of AOAC International, vol. 80, No. 2, 1997, pp. 408-417, XP000982223, Arlington, VA, USA., abstract.

K. Rinehart et al.: "Nodularin, microcystin, and the configuration of Adda." Journal of the American Chemical Society, vol. 110, No. 25, Dec. 7, 1988, pp. 8557-8558, XP002160425, Washington, D.C., USA.

J. Humphrey et al.: "Total synthesis of the serine-threonine phosphatase inhibitor microcystin-LA." Journal of the American Chemical Society, vol. 118, No. 47, Nov. 27 1996, pp. 11759-11770, XP002160426, Washington, D.C., USA.

J. Metcalf et al.: "Production of novel polyclonal antibodies against the cyanobacterial toxin microcystin-LR and their application for the detection and quantification of microcystins and nodularin." Water Research, vol. 34, No. 10, Jul. 2000, pp. 2761-2769, XP004203376, Amsterdam, Netherlands.

* cited by examiner

*Primary Examiner*—Mary E. Ceperley

(74) *Attorney, Agent, or Firm*—Weingarten, Schurgin, Gagnebin & Lebovici LLP

(57) ABSTRACT

The present invention relates to a protienaceous compound or functionally active derivative or part thereof having a binding site for a group represented by formula (I) which is part of a group of toxins derived from various cyanobacteria, to a method for its production, to diagnostic kits and to an affinty matrix (e.g. for use in immunoaffinity columns, online detection and purifications devices) containing the proteinaceous compound as well as to methods for substantially decreasing the amount of a compound containing the group represented by formula (I) in fluids or for concentrating compounds, e.g. toxins, containing the group represented by formula (I) from fluids such as crude water samples, extracts of algae or other tissue samples, e.g. to determine toxin concentrations.

14 Claims, 7 Drawing Sheets

Preparation of Anti-ADDA Antibody

Antibodies to the region of the molecule enclosed in the box are desired. Therefore, this part has been kept constant and the chemistry which is used to couple the the ADDA-hapten to the protein has to be varied in order to yield a suitable immunogen and antigen

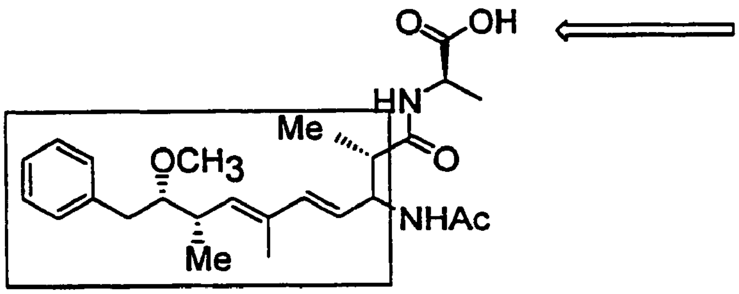

Point of conjugation to protein

N-Ac-ADDA-Gly-OH (1)

Or any other simpe amide

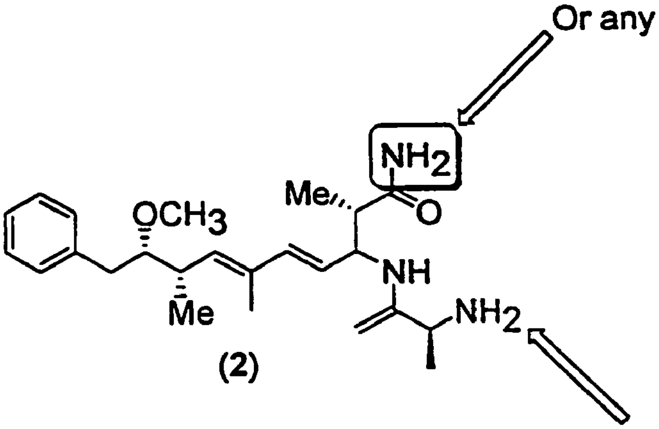

(2)

Point of conjugation to protein or

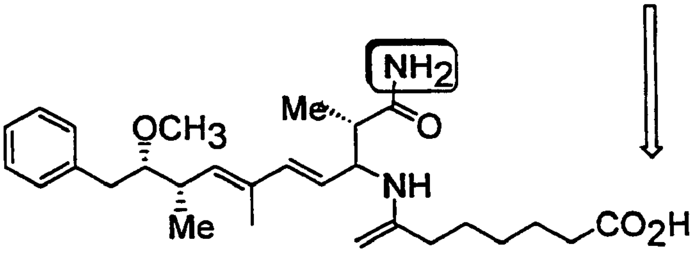

(3)

Glutarate derivative of amine

Fig. 2

| ADDA-Derivatives | |
|---|---|
| 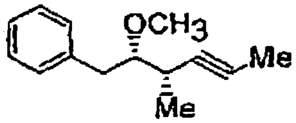 | Alkyne precursor<br>MW 202.32 |
| 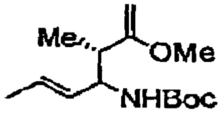 | "Vinyliodide" precursor<br>MW 369.23 |
| 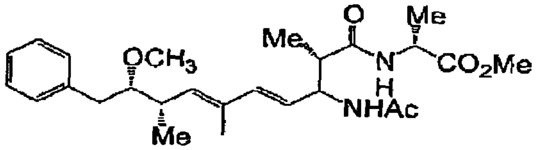 | "ADDA", N-acetyl, D-ala, methyl ester<br>MW 458.65 |
| 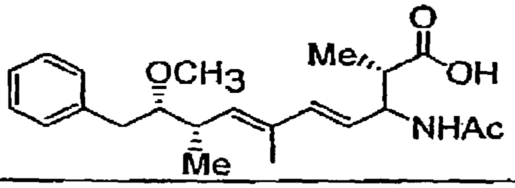 | "ADDA", N-acetyl, free acid<br>MW 373.54 |
| 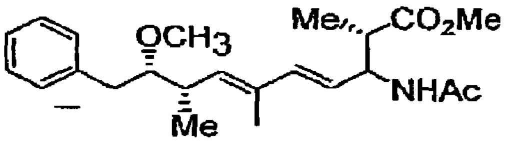 | "ADDA" N-acetyl, methyl ester<br>MW 387.57 |
| 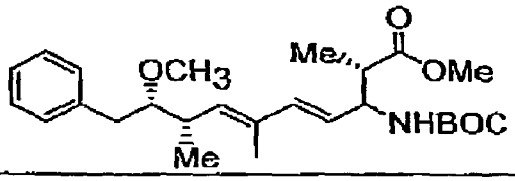 | "ADDA", BOC-amine, methyl ester<br>MW 445.66 |
| 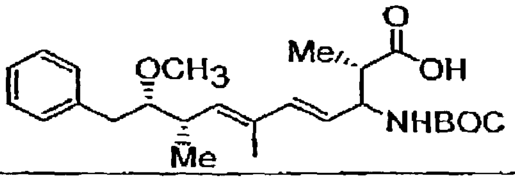 | "ADDA" BOC-amine, free acid<br>MW 431.63 |
Fig. 3

CONGENER INDEPENDENT DETECTION OF MICROCYSTIN AND NODULARIN CONGENERS

The present invention relates to a proteinaceous compound or functionally active derivative or part thereof having a binding site for a group represented by the following formula (I)

(I)

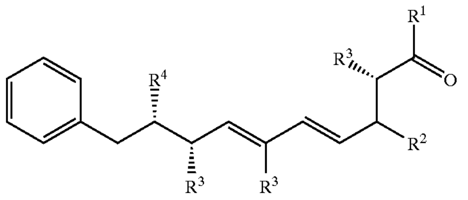

which is part of a group of toxins derived from various cyanobacteria, to a method for its production, to a diagnostic kits and to an affinity matrix (e.g. for use in immunoaffinity columns, online detection and purification devices) containing the proteinaceous compound as well as to methods for substantially decreasing the amount of a compound containing the group represented by formula (I) in fluids or for concentrating compounds, e.g. toxins, containing the group represented by formula (I) from fluids such as crude water samples, extracts of algae or other tissue samples, e.g. to determine toxin concentrations.

Due to increasing settlement, industrialisation and intensive agriculture wide spread problems of water pollution have arisen. This water pollution and the following eutrophication has led in many cases to the development of blooms of blue-green algae (i.e. cyanobacteria). The environmental factors which are responsible for the development of such blooms of cyanobacteria are up to now almost unknown. In general, blooms of cyanobacteria can be found in eutrophic bodies of water, e.g. under such conditions as relatively high nutrient levels (phosphate and nitrate), water temperatures of between 15 to 30° C. and pH-values of between 6 and 9 or higher (Wicks et al., 1990).

A severe problem of the development of blooms of cyanobacteria is that cyanobacteria produce a broad variety of toxic substances. Accordingly, since the end of the last century there has been an increasing number of cases of intoxication and even deaths of humans, animals, especially birds and fishes, which could be demonstrated to be caused by the use of water which was contaminated with cyanobacteria after chlorination and filtration for medical purposes (cases of deaths in the dialysis centers of Caruaru, Brazil, 1996 and Evora, Portugal, 1995), by the consumption of contaminated drinking water or even of clumps of cyanobacteria themselves (Francis, 1878; Falconer et al., 1983; Carmichael, 1984; Beasley et al., 1989; Mahmod et al., 1988; Skolberg et al. 1984).

The toxin producing cyanobacteria can be subdivided into species which synthesize mostly hepatotoxic peptides such as *Microcystis* sp., *Nodulara* sp. and *Oszillatoria* sp., and other genus which produce mostly neurotoxic alkaloids such as *Anabaena* and *Aphanizomenon* (Carmichael et al., 1990). Studies of different strains of *M.aeruginosa* revealed that, depending on strain and habitat, the cyanobacteria produce different congeners and amounts of a toxin (Sivonen et al., 1992 a–c).

Cyanobacteria can secrete the intracellularly produced toxins into the surrounding water (Watanabe et al., 1992 a,b). Further studies showed that the microcystin congener microcystin-LR is photostable, however, it can be microbially degraded (Watanabe et al., 1992 a; Tsuji et al., 1994; Cousins et al., 1996). Under aerobic conditions and in culture media which were inoculated with bacteria, the halflifetimes of microcystin-LR and -YR were more than 45 days (Watanabe et al., 1992 a). In contrast, half-lifetimes of less than 5 days were determined in seawater (Cousins et al., 1996). Under unfavorable conditions (i.e. cold temperatures and minimal presence of specific populations of microbes) microcystins may persist several days to even months and, therefore, may represent a potential danger for humans via the drinking water supply.

Accordingly, the increased incidence of gastroenteritis and liver carcinomas in humans has been attributed to the consumption of drinking water which was contaminated with cyanobacterial hepatoxins (in particular microcystin-LR) in several studies, although a direct relation between chronic microcystin-LR exposure and the development of liver carcinomas has not yet been proven (Tisdale, 1931; Keleti et al., 1981; Billings, 1981). Clinical indications of microcystin toxicoses in mammals is characterized by weakness, anorexia, mucous pallor, muscle termor, forced expirations and death by hypovolemic shock which is caused by intrahepatic hemorrhagia and/or liver failure (Theiss et al., 1988; Jackson et al., 1984).

Mammals seem to take up microcystin orally, and the toxin reaches the liver with the blood via a highly specific transporter mechanism (organic anion carrier) (Eriksson et al, 1990; Hooser et al., 1990; Runnegar et al., 1991). One molecular mechanism of the serious effects of microcystin seems to be its binding to the catalytic subunit of protein-phosphatases 1 and 2A which leads to their inhibition (Eriksson et al., 1990; Yoshezawa et al., 1990; Matsushima et al., 1990; Honkanen et al., 1990; McKintosh et al., 1990; McKintosh et al., 1995; Runnegar et al., 1996). After accute intoxication of high microcystin concentrations, the inhibition of proteinphosphatases leads to hyperphosphorylation of intermediate filaments which, in turn, is followed by collapse of the cytoskeleton, loss of the cells' structure, extensive intrahepatic hemorrhage and necrosis of the hepatocytes (Eriksson et al., 1990; Falconer et al., 1981, 1992). Similar to other proteinphosphatase inhibitors (e.g. calyculin-A, okadaic acid), the chronic exposure of mice to microcystin-LR leads to promotion of liver tumors (Falconer, 1991; Nishiwaki-Matsushima et al., 1992).

Due to the high toxicity and carcinogenicity of hepatotoxic cyanobacteria toxins and the potential chronic exposure of organisms (humans as well as animals) to these toxins via the drinking water there is an urgent need to detect toxic blooms of cyanobacteria early and to decrease the concentration of cyanobacteria toxins in drinking water.

Since it has been difficult to analytically and routinely detect the different microcystin and nodularin congeners with the required sensitivity (Kenefick et al., 1993; Lawton et al., 1994), prior art studies have concentrated on the destruction of the cyanobacteria toxins during the drinking water purification process. Mostly, continuous methods have been studied which can be carried out under routine conditions such as sand filtration, binding to activated carbon and destruction by chlorination (James et al., 1994). However, these studies revealed that neither sand filtration nor chlorination, UV-irradiation, treatment with hydrogen peroxide or potassium permanganate nor filtration via activated carbon could substantially remove the cyanobacteria toxins from drinking water. In this case a further problem seems to be the treatment of the raw water which is contaminated with cyanobacteria. The chlorination or the treatment of the cyanobacteria with copper sulfate leads to the release of the cyanobacteria toxins which are present in the cytosol without destroying the toxins to even the lowest degree. Also, the chlorination of sand filtered water is ineffective. Only the filtration via activated carbon seems to be appropriate to remove a considerable amount (about 60% to 80%) of the toxins. However, this purification performance was only reached for a limited period of time due to a relatively quick saturation of the activated carbon particles. Therefore, after about 10,000 bed volumes (1 bed volume=volume of the activated carbon) the filters became leaky.

Therefore, the technical problem underlying the present invention is to provide a novel system for the reliable detection as well as the removal of all kinds of hepatotoxic cyanobacteria toxins such as microcystin and nodularin congeners, particularly in and from, drinking water and other sources.

The solution to the above problem is provided by the embodiments of the present invention as characterized in the claims.

In particular, the present invention relates to a proteinaceous compound or functionally active derivative or part thereof having a binding site for a group represented by the following formula (I)

(I)

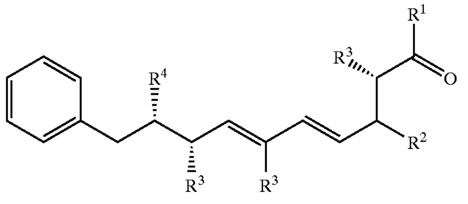

which is part of a toxin derived from a cyanobacterium, wherein group $R^1$ represents a halogen atom, preferably Br,—$OSO_3$, —OR' or —$NR'_2$ group $R^2$ represents hydrogen, $(C_1–C_4)$alkyl, $(C_1–C_4)$alkoxy, $(C_1–C_4)$acyl, $(C_1–C_4)$aminoacyl or $(C_1–C_4)$carboxaminoacyl, or the groups $R^1$ and $R^2$ are connected to each other to form a cyclic compound, the groups $R^3$ which may be the same or different are each independently selected from the group consisting of hydrogen and $(C_1–C_4)$alkyl,group $R^4$ represents $(C_1–C_4)$alkoxy, and wherein the phenyl group may be substituted or unsubstituted.

The term "proteinaceous compound or functionally active derivative or part thereof" means a compound which is capable of binding the above-described group of formula (I) and substantially consists of one or more polypeptides. The functionally active form of the proteinaceous compound according to the present invention may be a monomeric or a homo- or heterodimeric, -trimeric, -tetrameric or other oligomeric form.

The term "binding site" for the group as defined above means a three-dimensional arrangement of atoms of the above proteinaceous compound which is able to specifically interact with the group of formula (I) as defined above. The specific interaction may be any kind of chemical and/or physical interaction and comprises covalent binding, electrostatic interactions, hydrogen bonding, Van-der-Waals- as well as hydrophobic interactions.

Preferably, the group $R^1$ in the formula (I) represents independently from each other hydrogen, substituted or unsubstituted $(C_1–C_4)$alkyl or $(C_1–C_4)$acyl, when bound to nitrogen. According to a further preferred embodiment of the proteinaceous compound as defined above, the groups $R^3$ in the above formula (I) each represent methyl and group $R^4$ represents methoxy.

According to a further preferred embodiment of the proteinaceous compound of the present invention, group $R^1$ represents acylamino and group $R^2$ represents $(C_1–C_4)$acyl, or group $R^1$ represents glycyl or D-alanyl, respectively, and group $R^2$ represents acetyl, or group $R^1$ represents -$NH_2$ and group $R^2$ represents glutamidyl or 2-aminoproprionamidyl, respectively.

Preferably, the group represented by the above formula (I) is part of a toxin selected from the group consisting of microcystin and nodularin congeners. Microcystin (MC) and nodularin congeners are hereinafter referred to as microcystin-XY and nodularin-XY.

The chemical structures of *M. aeruginosa* and *Nodulaia* sp.-hepatotoxins (i.e. microcystin-XY and nodularin-XY) are described in several prior art studies (Botes et al., 1982 a, d, 1994, 1985; Rinehard et al., 1988). Microcystin-XY and nodularin-XY are cyclic peptides consisting of seven or five, respectively, amino acids. The following formula represents microcystin-LR.

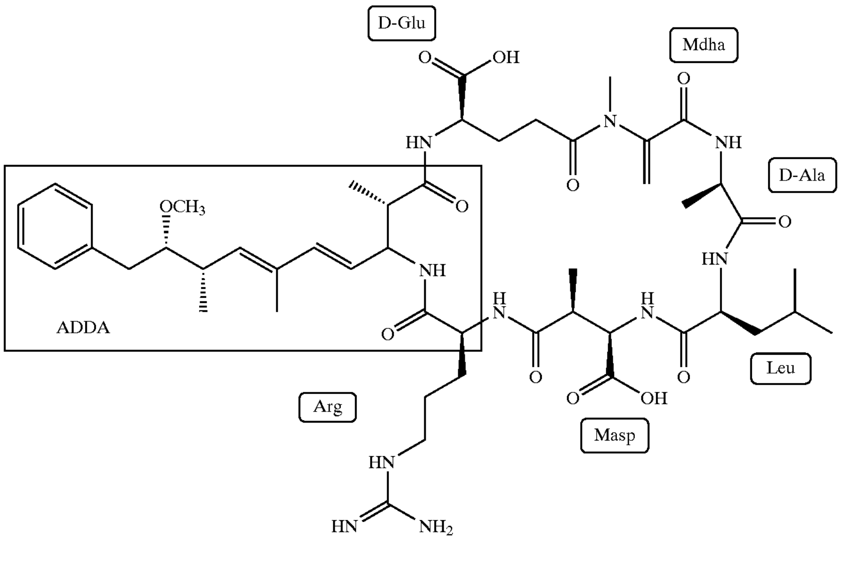

Nodularin-XY and microcystin-XY share the same specific characteristic amino acid (ADDA). The basic structure of microcystin-XY congeners consists of five non-variable amino acids: β-methylasparaginic acid, alanine, N-methyldehydroalanine, glutamate, and 3-amino-9-methoxy-2,6,8-trimethyl-1phenyldeca-4,6-dienic acid (ADDA). The differences between individual microcystin congeners are based on the two variable L-amino acids which are, for example, L-arginine and L-leucine in microcystin-LR and two times L-arginine in microcystin-RR, respectively. Normally, cyanobacteria produce a mixture of different forms of the toxins. The isolation of microcystin-XY from natural blooms of blue-green-algae resulted in up to six different microcystin congeners, and toxin concentrations up to 10 mg per 9 of dry mass of algae were determined (Wicks et al., 1990; Tsuji et al., 1994; Tencallar et al., 1994, 1995).

An especially preferred example of the proteinaceous compound according to the present invention is a polyclonal, monoclonal or recombinant antibody or a functionally active derivative or fragment thereof. The recombinant antibody may be produced by the translation and expression of any part of the genes coding for polyclonal or monoclonal antibodies and/or selection by screening of a phage display library using the group represent by the above formula (I).

The proteinaceous compound according to the present invention, e.g. a polyclonal, monoclonal or recombinant antibody or functionally active derivative or fragment thereof, has the advantage to be capable of binding to all congeners of the cyanobacterial hepatotoxins, e.g. microcystin and nodularin congeners which contain as a part of their structure the ADDA moiety.

In contrast to the proteinaceous compound of the present invention, the commercially available antibodies or ELISA kits, respectivley, are only capable of recognizing a very limited number of microcystin congeners. This means that the toxicity of blooms of cyanobacteria can be massively underdetermined by the use of the antibodies or kits, respectively, known so far.

A further embodiment of the present invention relates to a method for the preparation of the proteinaceous compound as defined above, comprising the steps of (a) preparing a compound containing a group represented by the formula (I) as defined above and (b) coupling the compound of step (a) to a carrier.

The "carrier" is not particularly limited to a specific embodiment and may be, e.g. any polymeric substance. For example, carriers which are suitable for the above method may be selected from the group consisting of polyethyleneglycol, proteins, polypeptides, polysaccharides and solid phase supports such as plastic supports. Preferably, the protein carrier is selected from bovine serum albumin (BSA), ovalbumin (OVA) cationised bovine serum albumin (cBSA), and horseradish peroxidase (HRP).

In another preferred embodiment of the present invention, the above method further comprises the steps of (c) immunizing an animal with the conjugate obtained in step (b) above and (d) isolating the animal's blood, blood serum and/or spleenocytes.

In a further preferred embodiment, the above method further comprises the steps of preparing antisera from the animal's blood serum obtained in the above step (d) for the preparation of polyclonal antibodies. According to another preferred embodiment, the method of the present invention further comprises the steps of preparing monoclonal antibody-producing hybridoma cells from the animal's spleenocytes obtained in the above step (d). Yet another preferred embodiment of the above-defined method comprises the further steps of preparing recombinant antibodies including the isolation of the genetic material (DNA) from cells present in the animal's blood or from antibody-producing hybridoma cells.

A further embodiment of the present invention relates to a diagnostic kit containing the proteinaceous compound as defined above.

Another embodiment of the present invention relates to an affinity matrix containing the proteinaceous compound as defined above coupled to a polymeric resin.

The proteinaceous compound according to the present invention, e.g. a polyclonal, monoclonal or recombinant antibody or a functionally active derivative or fragment thereof as defined above, is particularly useful for the detection of a compound containing the group represented by the above formula (I), for concentrating the toxins from crude extracts prior to analysis to determine toxin concentrations as well as to substantially decrease the amount of a compound containing the group represented by the formula (I) in a fluid, pharmaceutical or food preparation.

Therefore, a further embodiment of the present invention relates to a method for concentrating a compound containing the group represented by the formula (I), e.g. a toxin, from a fluid such as crude water samples, extracts of algae or other tissue samples, or for substantially decreasing the amount of a compound containing the group represented by the formula (I) in a fluid, e.g. water such as hemodialysis water, drinking water or water derived from rivers, lakes and oceans, comprising the steps of (a) preparing the proteinaceous compound as defined above, (b) coupling the compound obtained in step (a) to a polymeric matrix, and (c) contacting the fluid with the polymeric matrix obtained in step (b).

Furthermore, the above method may also be applied to the cleaning of any other sources of cyanobacteria toxins such as, for example, food stuffs.

The Figures show:

FIG. 2 is a diagram showing preferred strategies for the coupling of an ADDA-hapten to a protein.

FIG. 3 shows several ADDA-derivatives which were synthesized for the production of the antibody useful for congener independent detection of microcystin and nodularin congeners.

Figure 1:
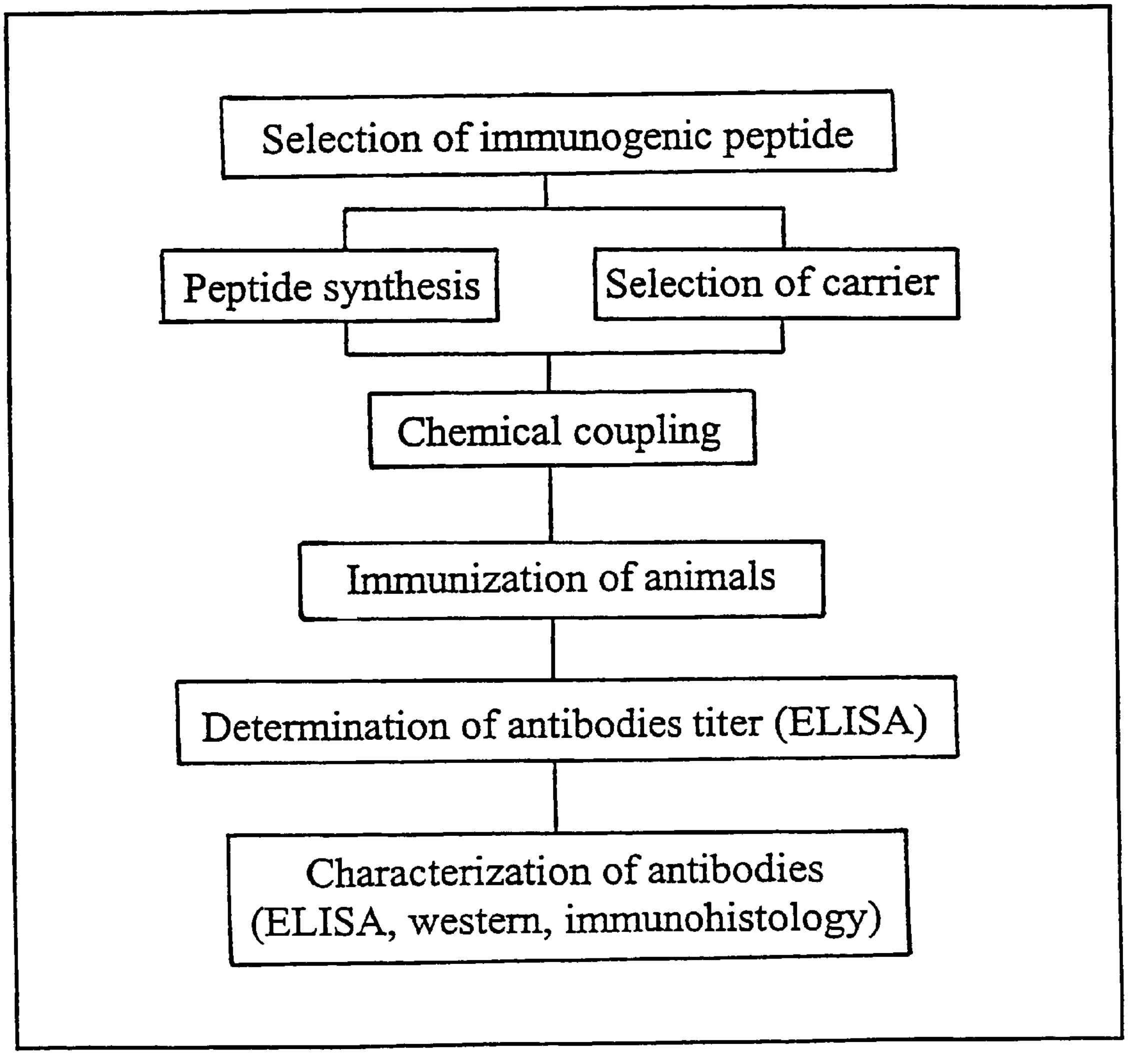
FIG. 1 is a diagram showing a flow chart for the strategy of preparation of an anti-ADDA antibody according to the present invention.

The present invention is further illustrated by the following non-limiting examples.

EXAMPLE

ADDA Hapten Synthesis

The starting material N-Boc-ADDA-Me (35) was prepared by the published route: Humphrey, J. M.; Aggen, J.; Chamberlin, A. R. *J. Am Chem. Soc.* 1996, 118, 11759–11770. "Synthesis of the Serine-threonine Phosphatase Inhibitor Microcystin LA."

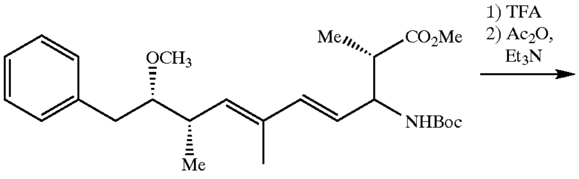

N-Boc-Adda-OMe (35)

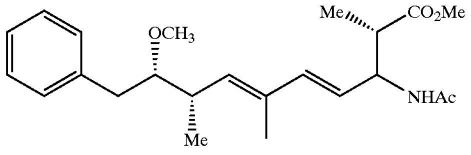

N-Boc-Adda-OMe

N-Ac-ADDA-OMe. To 31 mg (0.70 mmol) of Boc-ADDA-OMe in a flask was added 2 ml of TFA. After one hour the TFA was removed under vacuum, and the residue was concentrated three times from toluene to remove the TFA. The resulting oil was dissolved in 2.5 ml of freshly distilled $CH_2Cl_2$, and this was cooled to 0° C. 28 mg (0.28 mmol) of anhydrous triethylamine was added to the solution, followed by 0.141 g (1.39 mmol) of freshly distilled acetic anhydride. One hour later 5 ml of saturated $NH_4Cl$ was added, and the mixture was stirred for 20 minutes at 0° C. The mixture was partitioned between water and EtOAc, and the phases were separated. The aqueous phase was extracted twice with EtOAc. The combined organic phases were washed once each with 50% saturated $NH_4Cl$, 50% saturated $NaHCO_3$, and brine, dried over $MgSO_4$, filtered, and concentrated under vacuum to give a white solid. The solid was purified via flash chromatography (1/1 EtOAc/hexanes) to give 25 mg (93%) of a white solid: $R_f$ 0.23 (40:60 EtOAc:hexanes); IR (thin film) 3330, 2919, 1731, 1654, 1454 $cm^{-1}$; $^1$HNMR (500 MHz, $CDCl_3$) 0/00 0.99 (d, J=6.5, 3H), 1.20 (d, J=7, 3H), 1.57 (s, 3H), 2.02 (s, 3H), 2.58 (ddq, J=6, 6.5, 10 Hz, 1H), 2.67 (dd J=7.5, 14 Hz, 1H), 2.78 (obscured mult., 3H), 2.79 (dd, J=5, 13.5 Hz, 1H), 3.17 (ddd, J=5, 6, 7 Hz, 1H), 3.21 (s, 3H), 3.65 (s, 3H), 4.71 (ddd, J=4.5,5,5.5 Hz, 1H), 5.37 (d, J=9.5 Hz, 1H), 5.42 (dd, J=15.5, 6.5 Hz, 1H), 6.18 (d, J=15.5 Hz, 1H), 6.40 (d, J=9 Hz, 1H), 7.25-7.15 (m, 5H); $^{13}$C NMR (125 MHz, $CDCl_3$) 0/00 175.8, 169.5, 139.5, 136.6, 136.3, 132.4, 129.5, 128.2, 126.0, 124.9, 87.1, 58.6, 3.0, 51.7, 43.6, 38.4, 36.8, 23.5, 16.2, 14.9, 12.7; HRMS calculated for $C_{23}H_{34}NO_4$ $(M+H)^+$: 388.2488. Found: 388.2505.

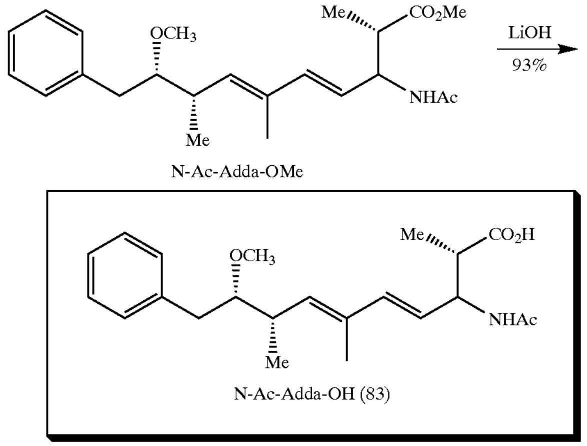

N-Ac-Adda-OMe
N-Ac-Adda-OH (83)

N-Ac-ADDA-OH. To 22 mg (0.057 mmol) of the protected ADDA-derivative in 2 ml THF was added 0.57 ml (0.57 mmol) of 1 M LiOH. After 22 hours the mixture had clarified, and it was partitioned between hexanes and water. The phases were separated, and the aqueous phase was washed once with hexanes. The combined organic phases were back-extracted three times with water. The combined aqueous phases were acidified with 1 M $NaHSO_4$, and extracted three times with $CH_2Cl_2$. The combined $CH_2Cl_2$ phases were washed once with brine, filtered through cotton, and concentrated to give 23 mg of 83 as an oil that was taken on without purification: $R_f$ 0.34 (1:49:50 HOAc:EtOAc: hexanes); IR (thin film) 3295 br, 2923, 1713, 1640 $cm^{-1}$; $^1H$ NMR (500 MHz, $CDCl_3$) % 0.99 (d, J= 6.5, 3H), 1.25 (d, J=7, 3H), 1.58 (s, 3H), 2.02 (s, 3H), 2.57 (ddq, J=6.5, 6.5, 9.5 Hz, 1H), 2.65 (dd J=7.5, 14 Hz, 1H), 2.76 (par.obsc. m, 3H), 2.77 (dd, J=5, 13 Hz, 1H), 3.17 (ddd, J=5, 6.5, 6.5 Hz, 1H), 3.21 (s, 3H), 4.71 (ddd, J=5, 6, 10 Hz, 1H), 5.37 (d, J=9.5 Hz, 1H), 5.45 (dd, J=15.5, 6.5 Hz, 1H), 6.18 (d, J=15.5 Hz, 1H), 6.37 (d, J=9.5 Hz, 1H), 7.25-7.15 (m, 5H); HRMS calculated for $C_{22}H_{32}NO_4(M+H)^+$:374.2331, Found: 374.2325.

N-Ac-Adda-OH (83)

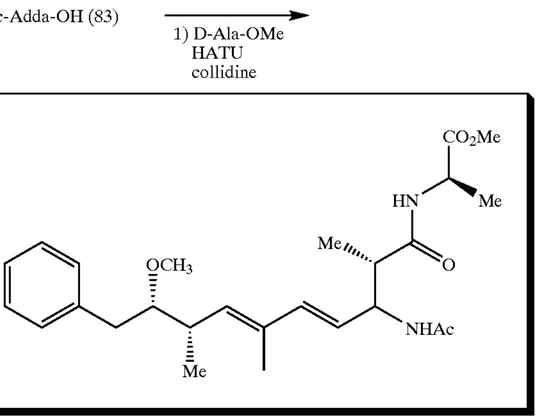

N-Ac-ADDA-D-Ala-OMe. To 17 mg (0.12 mmol) of D-Ala-OMe hydrochloride and 14 mg (0.036 mmol) of HATU in a flask was added 9 mg (0.024 mmol) of 83 in 0.6 ml DMF. The resulting solution was cooled to 0° C., and 41 mg (0.34 mmol) of collidine was added. The solution was stirred at 0° C. for 2 hours, followed by warming to room temperature and stirring overnight. The mixture was partitioned between water and EtOAc, and the phases were separated. The aqueous phase was extracted once with EtOAc. The combined organic phases were washed once each with sat. $NaHCO_3$, water, 1 M $NaHSO_4$, water, and brine, dried over $MgSO_4$, filtered, and concentrated under vacuum to an off-white solid. Chromatography (80:20 EtOAc:hexanes) gave 8 mg (73%) of a white solid: $R_f$ 0.17 (60:40 EtOAc:hexanes); IR (thin film) 3284, 3067, 2923, 1743, 1650, 1542 $cm^{-1}$; $^1H$ NMR (500 MHz, $CDCl_3$) 0/00 0.99 (d, J=6.5, 3H), 1.23 (d, J=7, 3H), 1.35 (d, J=7 Hz, 3H), 1.58 (s, 3H), 2.04 (s, 3H), 2.52 (dq, J=4, 7 Hz, 1H), 2.59 (ddq, J=6.5, 7, 9.5 Hz, 1H), 2.68 (dd J=7.5, 14 Hz, 1H), 2.81 (dd, J=4.5, 14 Hz, 1H), 3.19 (ddd, J= 5, 7, 7 Hz, 1H), 3.22 (s, 3H), 3.75 (s, 3H), 4.55 (dq, J=7,7 Hz, 1H), 4.62 (m, 1H), 5.39 (d, J=9.5 Hz, 1H), 5.45 (dd, J=15.5, 6.5 Hz, 1H), 6.18 (d, J=15.5 Hz, 1H), 6.23 (d, J=7 Hz, 1H), 7.05 (d, J=9 Hz, 1H), 7.27-7.17 (m, 5H); $^{13}C$ NMR (125 MHz, $CDCl_3$) 0/00 12.7, 15.4, 16.2, 18.4, 23.5, 36.7, 38.2, 44.4, 47.9, 52.6, 53.7, 58.6, 86.9, 125.2, 125.9, 128.2, 129.4, 132.2, 136.2, 139.4, 169.9, 173.2, 174.6; HRMS calculated for $C_{26}H_{39}N_2O_5$ $(M+H)^+$:459.2859, Found:459.2869.

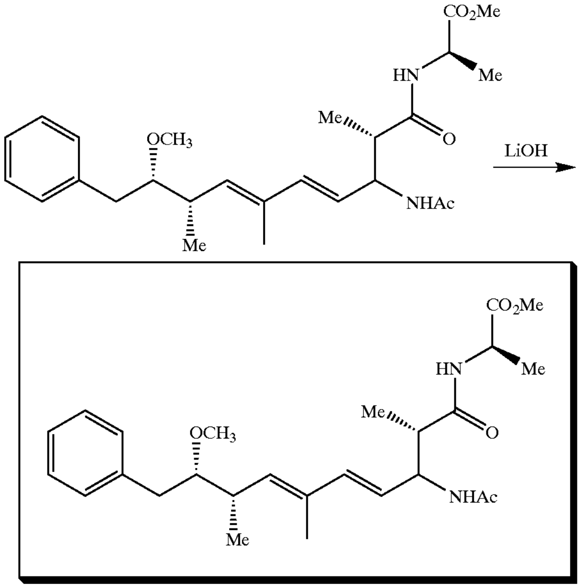

N-Ac-ADDA-D-Ala-OH. To 5 mg (0.01 1 mmol) of N-Ac-ADDA-D-Ala-OMe in 1.7r) ml of THF was added 0.10 ml (0.10 mmol) of 1 M LiOH. After 50 minutes, the mixture was partitoned between ether and water, and the phases were separated. The aqueous phase was washed once with ether. The combined etheral phases were back-extracted three times with water, and the combined aqueous phases were acidified to pH=3 with saturated citric acid. The aqueous phases were then extracted twice with EtOAc, and the combined EtOAc phases were washed twice with water, once with brine, dried over $MgSO_4$, filtered, and concentrated in vacuo. The resulting solid was purified by preparative reversed-phase HPLC, retention time of product =15.7 minutes (70 MeOH/30 0.2% aq. TFA), to give 4 mg (85%) of the title compound as a white solid: $R_f$ 0.36 (1 HOAc/10 MeOH/89 $CH_2Cl_2$); IR (thin film) 3288 br, 2937, 1720, 1658,1632 $cm^{-1}$; $^1H$ NMR (500 MHz, DMSO-$d_6$) 0/00 0.94 (d, J=7.0 Hz, 3H), 0.96 (d, J=7.0 Hz, 3H), 1.19 (d, J=7.0 Hz, 3H), 1.52 (s, 3H), 1.82 (s, 3H), 2.63 (dd, J=7.0, 14.0 Hz, 1H), 2.73 (dd, J=5.0, 14.0 Hz, 1H), 3.16 (s, 3H), 3.22 (ddd, J=5.5, 5.5, 6.5 Hz, 1H), 4.19 (dq, J=7.0, 7.5 Hz, 1H), 4.40 (m, 1H), 5.38 (d, J=10.0 Hz, 1H), 5.44 (dd, J=6.5, 16.0 Hz, 1H), 6.05 (d, J=16.0 Hz, 1H), 7.17 (d, J=7.5 Hz, 3H), 7.25 (t, J=7.5 Hz, 2H), 7.60 (d, J= 9.0 Hz, 1H), 8.01 (d, J=7.0 Hz, 1H); FAB MS calculated for $C_{25}H_{37}N_2O_5(M+H)^{+}$: 445.2702. Found: 445.2695.

Coupling of Hapten to Proteins

Preparation of BSA-, cBSA-, and OVA-N-AcADDA-AlaOH.

BSA (10.6 mg), cationised BSA (cBSA) (10.0 mg), and OVA (8.3 mg) were each dissolved in PBS (1000 μl). Carbonyidiimidazole (19.81 mg, 0.12 mmol) was dissolved in dry DMF (500 μl), and a portion of the solution (100 μl) was added to N-acetyl-ADDA-D-Ala-OH (1.0 mg, 2.2 μmol) and allowed to stand for 90 min. DMF was added (BSA, 260 μl; cBSA, 260 μl; OVA, 280 μl) to the protein solutions just prior to addition of the activated ADDA-derivative. The solution of the activated ADDA-derivative (40 μl each to the BSA and cBSA, 20 μl to the OVA) was then added to the protein solutions, and the reaction was allowed to proceed at 4° C. for about 16 h. The resulting conjugates were repeatedly diluted and then concentrated by ultrafiltration (Filtron centrifugal ultrafiltration tubes, 10 K cutoff) until the calculated dilution of unretained low molecular weight compounds was >$10^6$.

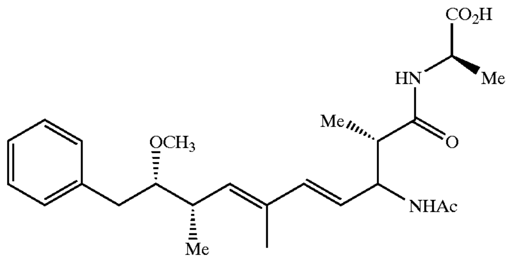

N-Ac-Adda-D-Ala-OH

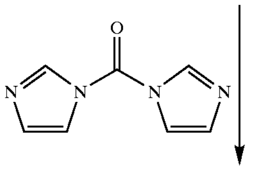

-continued

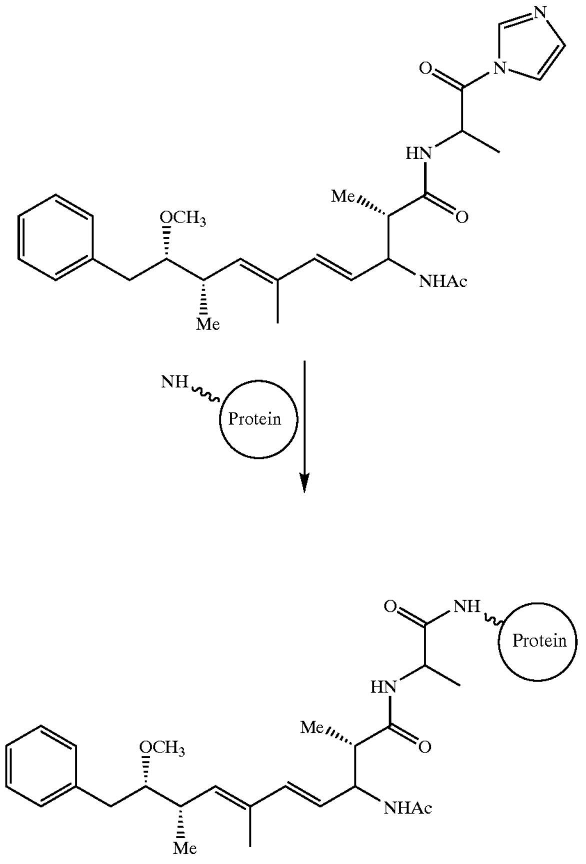

N-Ac-Adda-D-Ala-Protein Conjugate

Preparation of HRP-MC-YR and aminoHRP.

Horse radish peroxidase (HRP) was oxidized by the method of Hermanson. HRP (19.73 mg, Boehringer) was dissolved in PBS and cooled to 4° C. $NaIO_4$ (36.7 mg) was dissolved in water (2 ml), and 100 μl of this was added to the HRP solution, which rapidly became green. The reaction was held at 4° C. in the dark for 20 min, then the HRP was separated from low molecular weight material by elution with PBS through a desalting column (Bio-Rad Econo-Pac 10DG).

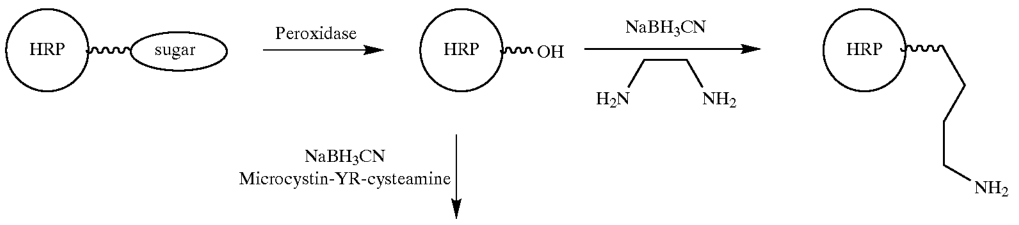

-continued

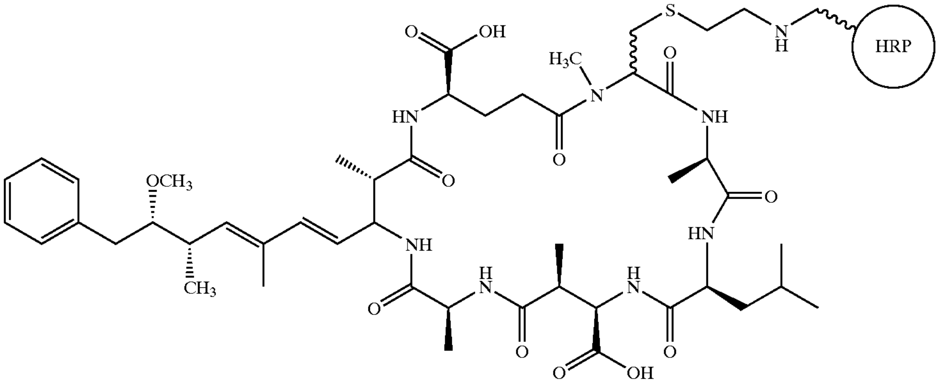

To half of the oxidized HRP MC-YR-cysteamine (51 μg, see below) was added in MeOH (50 μl). To the other half diaminoethane hydrochloride (500 mg) was added in PBS (500 μl). $NaBH_3CN$ (16.4 mg) was dissolved in PBS (500 μl), and 100 μl of this was added to each HRP reaction (which immediately became crimson). After standing at 4° C. in the dark for about 16 h, the reactions were quenched by addition of diethanolamine in PBS (50 μl of 300 μl of diethanolamine in 5 ml PBS) and allowed to stand at 4° C. in the dark for 2 h. The HRP solutions were then purified by passing through desalting columns (as above). The diaminethane conjugate (henceforth referred to as amino-HRP) and MC-YR conjugates were further purified by ultrafiltration to >$10^{4}$ dilution (as above).

Preparation of HRP-, aminoHRP-, and OVA-ADDA-HG.

HRP, aminoHRP, and OVA were each dissolved in PBS (1 ml). To ME-ADDA-HG (0.67 mg) was added CDl (1.16 mg) in dry DMF (100 μl), and the reaction proceeded at ambient temperature 1.5 h whereupon dry DMF (150 μl) was added. A portion of this solution was added to the solutions of the proteins (50 μl to aminoHRP, 100 μl to HRP and OVA). DMSO (200 μl) was then added to the HRP and OVA reactions to assist in solubilising the reactants, and the three reactions were maintained at 4° C. in the dark for ca 16 h. The conjugates were then purified on the desalting column and then further purified by repeated ultracentrifugation to >$3\times10^{4}$ dilution (as above).

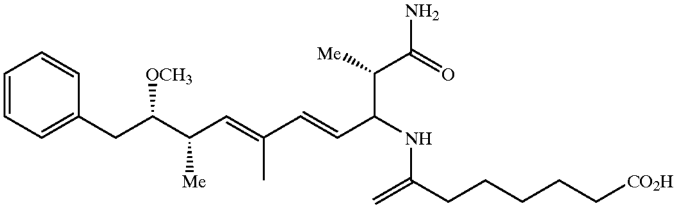

(3)

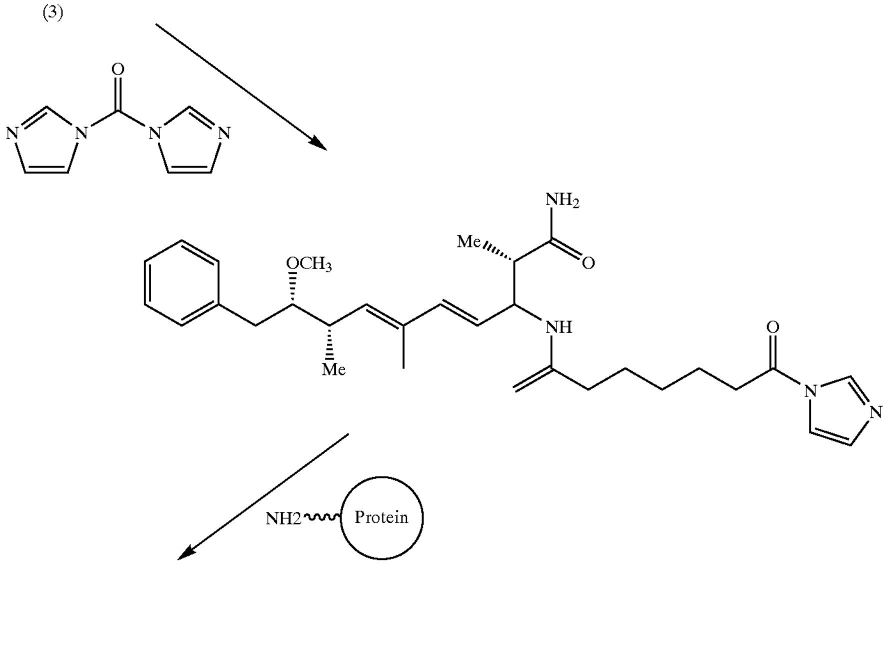

-continued

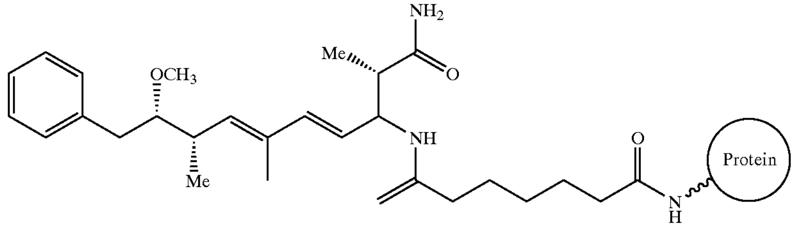

Preparation of MC-YR-cysteamine conjugate

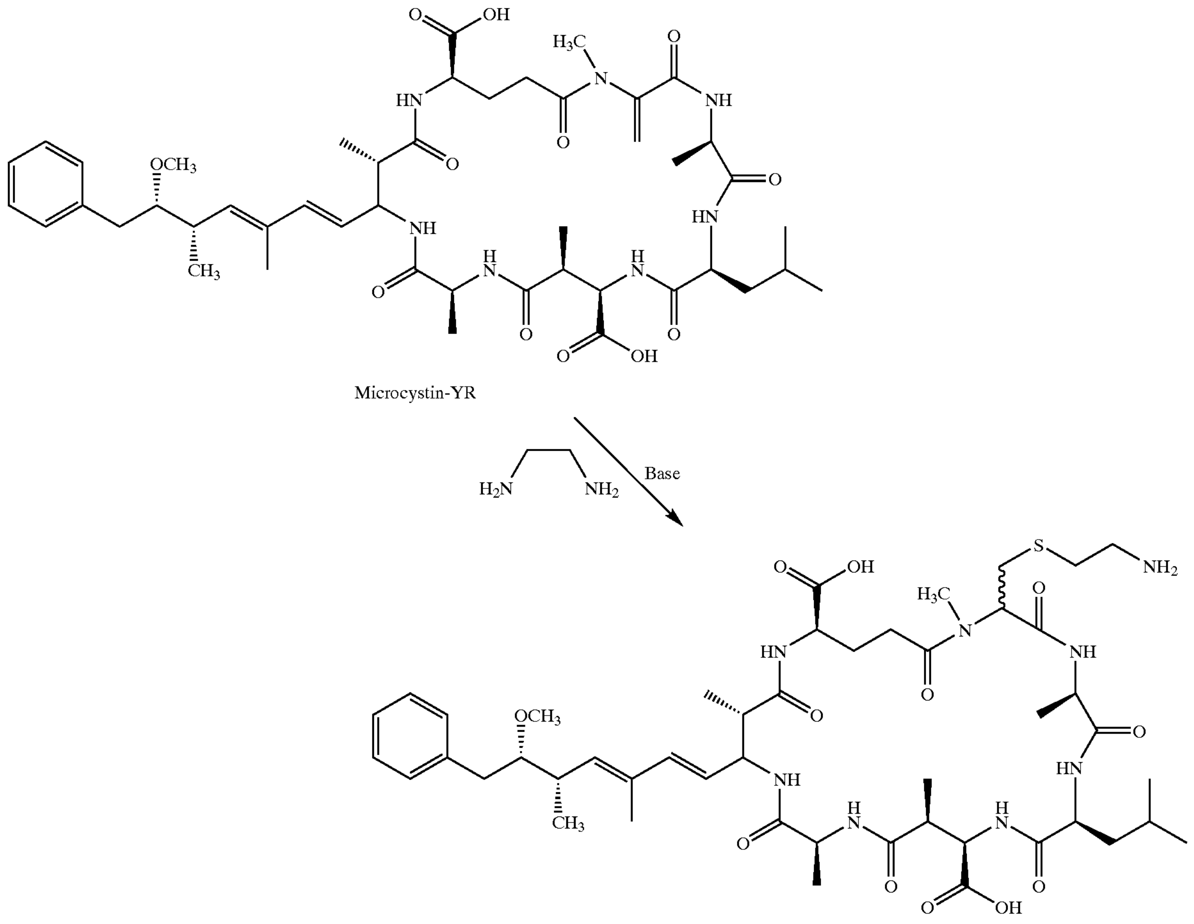

Microcystin-YR

Microcystin-YR-cysteamine conjugated

The method is based on those of Kondo et al. (1992) and Sherlock et al. (1998). Cysteamine (15.6 mg) was dissolved in water (500 μl), and MC-YR (500 μg) was dissolved in 5% $K_2CO_3$ (500 μl). The cysteamine solution (50 μl, followed by 100 μl at 30 min) was added to the MC-YR solution in portions. After about 2 h the reaction was acidified to pH 3 to 4 and applied to a reverse-phase flash column (4×1 cm). The column was eluted successively with water (10 ml), 10% MeOH (10 ml), 20% MeOH (10 ml), 30% MeOH (10 ml), 50% MeOH (2×10 ml), 70% MeOH (2×10 ml), and MeOH (3×10 ml). HPLC analysis indicated the product to be in the 50% MeOH and the first of the 70% MeOH fractions. These fractions were combined and the solvent removed in vacuo to yield MC-YR-cysteamine as a colourless solid (204 μg). ESI-MS mlz 1121.9 (M-H$^-$); $^1H$, COSY and HMBC NMR spectra were consistent with the desired product.

Immunization of sheep and mice with ADDA-protein conjugates

Nine sheep and nine mice were immunised with the above BSA-ADDA-, cBSAADDA- and OVA-ADDA-conjugates (three animals for each conjugate). One mg of each conjugate in a volume of 1 ml phosphate buffer saline was added to Freund's complete adjuvants in case of the primaryinjection and homogenised to form an emulsion, and Freunds incomplete adjuvants in the case of booster injections. The animals received a minimum of three boosts in case of sheep, and six boosts in case of mice at approximately 4-week intervals.

ELISA

Indirect ELISA using polyclonal antibody #824

Figure 5:
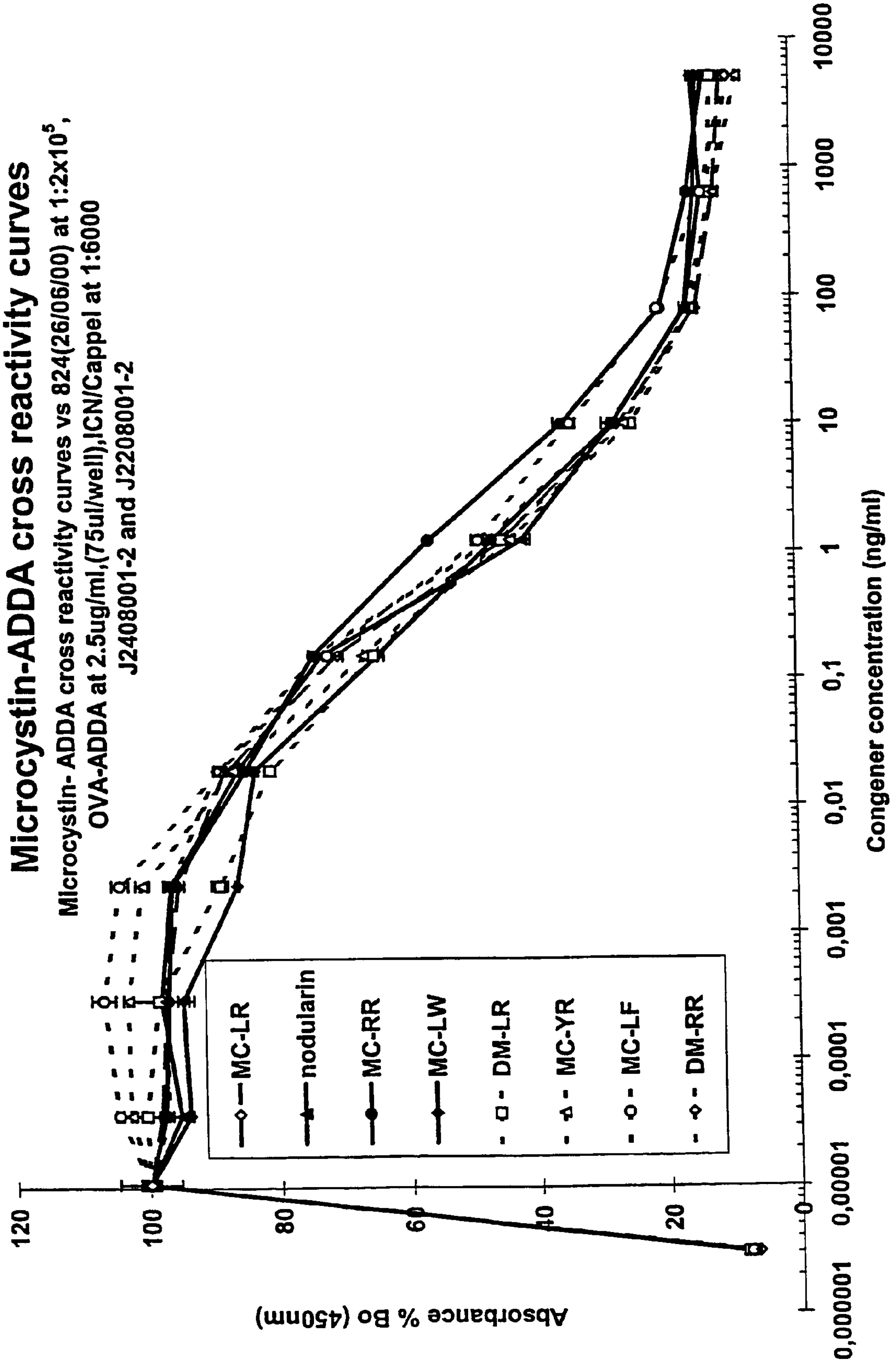
FIG. 5 is a diagram showing the crossreactivity with respect to different microcystin congeners (MC-LR, -RR and -YR) and nodularin of the ant-ADDA antibody (ADDA-824new, i.e. 26/06/00) raised in sheep which is directed against ADDA-HG coupled to ovalbumin.

ELISA plates (NUNC MaxiSorp 1 #439454, Denmark) were coated with OVA-Nacetyl-D-alanyl-ADDA conjugate (OVA-ADDA-HG3/99') in 0.05 M sodium bicarbonate buffer pH 9.6 (75 μl, 2.5 μg/ml) overnight at 22° C. (RT). After a wash with PBS, additional binding sites were blocked by incubation with OVA (1/% w/v, 300 μl, 1 h, 20–25° C.). Plates were washed two times with PBS and used immediately or stored at 4° C. for up to 7 days. In the assay, sample or standard (50 μl) was added to the wells together with antiserum (50 μl) at the appropriate dilution (e.g. sheep serum #824$^{26/6/00}$ at 1/200 000; cf. FIG. 5). After incubation at 20–25° C. for 2 h, wells were washed twice with PBS +0.05% Tween® 20 (PBST) and twice with PBS. Secondary antibody, horse radish peroxitase conjugated antispecies antibody, e.g. ICN/Cappel Anti-sheep-HRP (100 μl, 1/6000), was then added to the wells and incubated for 2 h. Thereafter, wells were aspirated, washed twice with PBST and twice with PBS. TMB substrate solution, prepared by adding 110 μl TMB stock (10 mg/ml in DMSO) to 11 ml of sodium acetate buffer (0.1 M, pH 5.5) containing 0.005% $H_2O_2$, was then added and incubated for 15 minutes. The reaction was stopped by addition of $H_2SO_4$ (50 μl, 2 M), and the absorbance at 450 nm was determined with a microplate spectrophotometer. Standards and samples were prepared for ELISA by dilution in the following diluents: (i) methanol in PBS to a maximum methanol concentration of 10% (v/v); (ii) PBS; (iii) lake water (Lake Constance, Germany); (iv) tap water; (v) river water, Waikato River, New Zealand. All samples were analysed in at least duplicate, and over a range of dilutions.

ELISA method using antibody ADDA-#824$^{26/6/00}$ in detail

Figure 4:
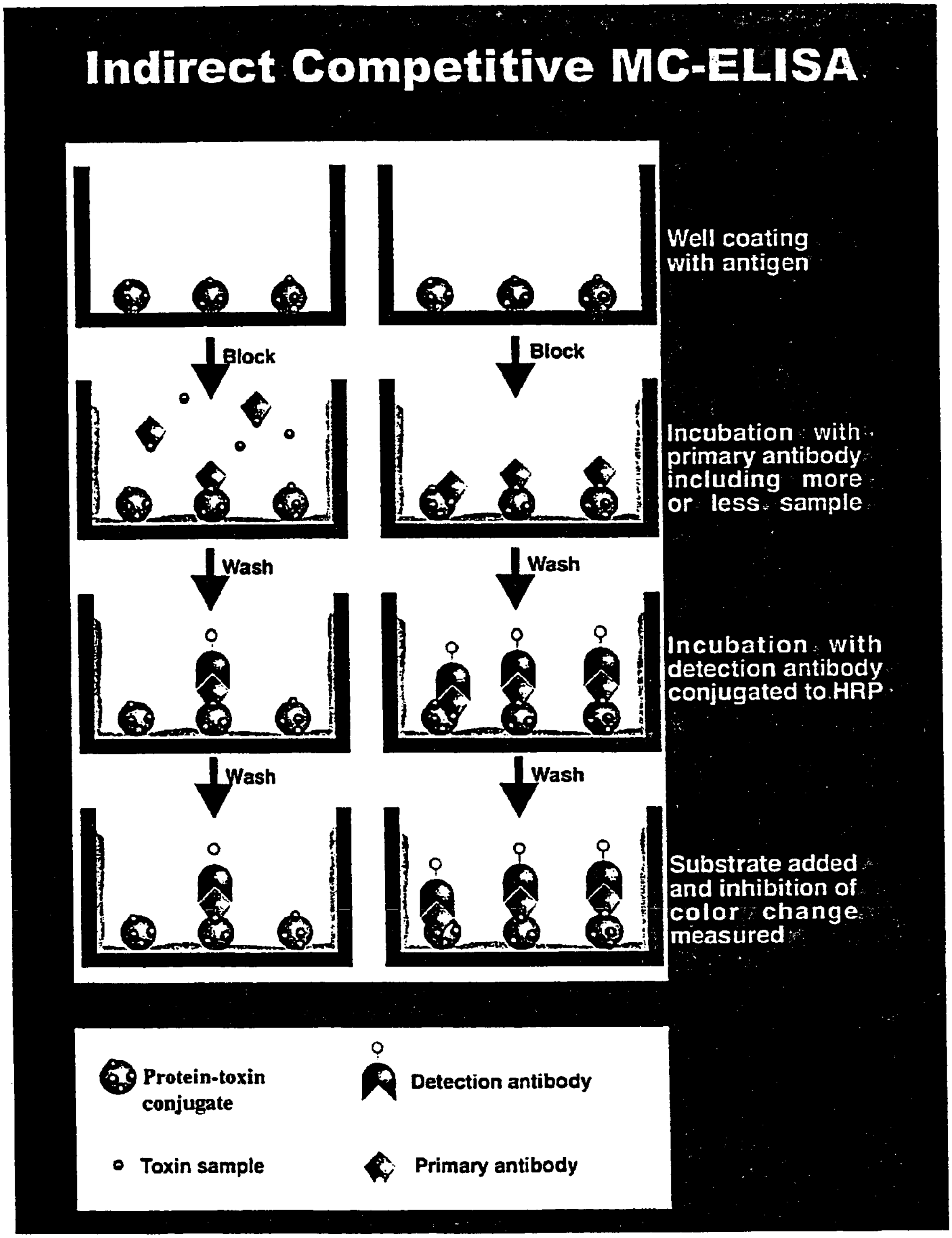
FIG. 4 is a diagram showing the general principle of the indirect competitive microcystin enzyme-linked immunosorbent assay (MC-ELISA).

The principle of the indirect competitive microcystin ELISA (MC-ELISA) employed is shown in FIG. 4. This method comprises the following steps:

1. Prepare antigen (OVA-ADDA-HG$^{3/99}$) in bicarbonate buffer, pH 9.6 at 2.5 μg/ml (5 ml +/plate).
2. Coat antigen onto microtitre plate at 75 μl/well, tap to mix and cover, incubate overnight at room temperature (RT, 22° C.).
3. Wash two times in PBS, aspirate.
4. Block plate with 1% OVA (no. A-5503 from Sigma) (300 μl for 1 hour at RT (22° C.).
5. Wash two times in PBS, aspirate and use immediately or add 2–300 μl PBS for storage. The plates can be stored at this stage in PBS (at 4° C.) for up to 7 days.
6. Add 50 μl sample, or standard, in PBS; and 50 μl of antibody ADDA-#824$^{26/6/00}$ (developed in sheep) at 1/200 000 dilution in OVA-blocker and incubate for 2 hours at RT (22° C.). Standard curve: Primary 5000 ng/ml, then nine serial 1:8 dilutions (1+7) in 10%MeOH/PBS.
7. Wash two times in PBS/Tween, two times in PBS.
8. Add 100 μl of secondary antibody conjugate diluted in OVA (peroxidase conjugated rabbit-anti-sheep lgG (ICN #55814) at a final dilution of 1/6000 and incubate for 2 hours at RT (22° C.).
9. Wash two times in PBST, two times in PBS, aspirate.
10. Turn on plate reader—needs a 15 minute warm up before reading at step 13.
11. Add 100 μl of substrate. Incubate for 15 minutes at RT (22° C.) until colour develops.
12. Add 50 μl stop solution (2M $H_2SO_4$).
13. Read absorbance at 450 nm. Note that the absorbance at 655 nm can be measured prior to adding the stop solution if required.

Direct ELISA using polvclonal antibody #825

ELISA plates (NUNC Maxisorp 1 #439454, Denmark) were coated with the appropriate antiserum (#825$^{14/12/98}$) in 0.05 M sodium bicarbonate buffer pH 9.6 (50 μl, 1/20 000) overnight at 20° C. After a 2×PBS wash, additional binding sites were blocked by incubation with BSA (1% w/v, 300 μl, 1 h, 20–25° C.). Plates were washed two times with PBS and used immediately or stored at 4° C. for up to 7 days. In the assay, sample or standard (50 μl) was added to the wells together with the appropriate hapten-enzyme conjugate (50 μl, $NH_2$-ADDA-HRP$^{3/99}$, 200ng/ml). After incubation at 20–25° C. for 3 hours, wells were washed twice with PBST and twice with PBS. TMB substrate solution, prepared by adding 110 μl TMB stock (10 mg/ml DMSO) to 11 ml sodium acetate buffer (0.1 M pH 5.5) containing 0.005% $H_2O_2$, was then added, followed by incubation for 15 minutes. The reaction was stopped by addition of $H_2SO_4$ (50 μl, 2 M), and the absorbance was determined with a microplate spectrophotometer at a wavelength of 450 nm. Standards and samples were prepared for ELISA by dilution in the following diluents: (i) methanol in PBS to a maximum methanol concentration of 10% (w/v); (ii) PBS; (iii) lake water (Lake Constance, Germany); (iv) tap water; (v) river water (Waikato River, New Zealand). All samples were analysed at least in duplicate and over a range of dilutions.

Direct ELISA method in detail (example 99153005).

1. Prepare antiserum (#825, developed in sheep) in bicarbonate buffer pH 9.6 at 1/20 000 (5 ml\plate). Coat microtitre plate with 50 μl antiserum per well, tap to mix and cover, incubate overnight at room temperature (RT, 22° C.).
2. Wash 2×PBS, aspirate.
3. Block plate with 1% BSA (300 μl for 1 h at RT (22° C.)).
4. Wash 2×PBS, aspirate and use or add 200–300 μl PBS for storage. The plates can be stored at this stage in PBS (at 4° C.) for up to 7 days.
5. Add 50 μl sample, or standard in PBS, and 50 μl of hapten-enzyme conjugate ($NH_2$-ADDA-HRP) 200 ng/ml in BSA-blocker and incubate at room temperature for 3 hours at RT (22° C.). Standard curve primary 2000 ng/ml, then 9 serial 1:6 dilutions in PBS.
6. Wash 2×PBST, 2×PBS. A*spirate*.
7. Turn on plate reader—needs a 15 minute warm up before reading at step 10.
8. Add 100 μl of substrate. Incubate at RT (22° C.) for 15 minutes.
9. Add 50 μl stop solution (2 M $H_2SO_4$).
10. Read absorbance at 450 nm. Note that the absorbance at 655 nm can be measured prior to adding the stop solution if required.

Figure 6:
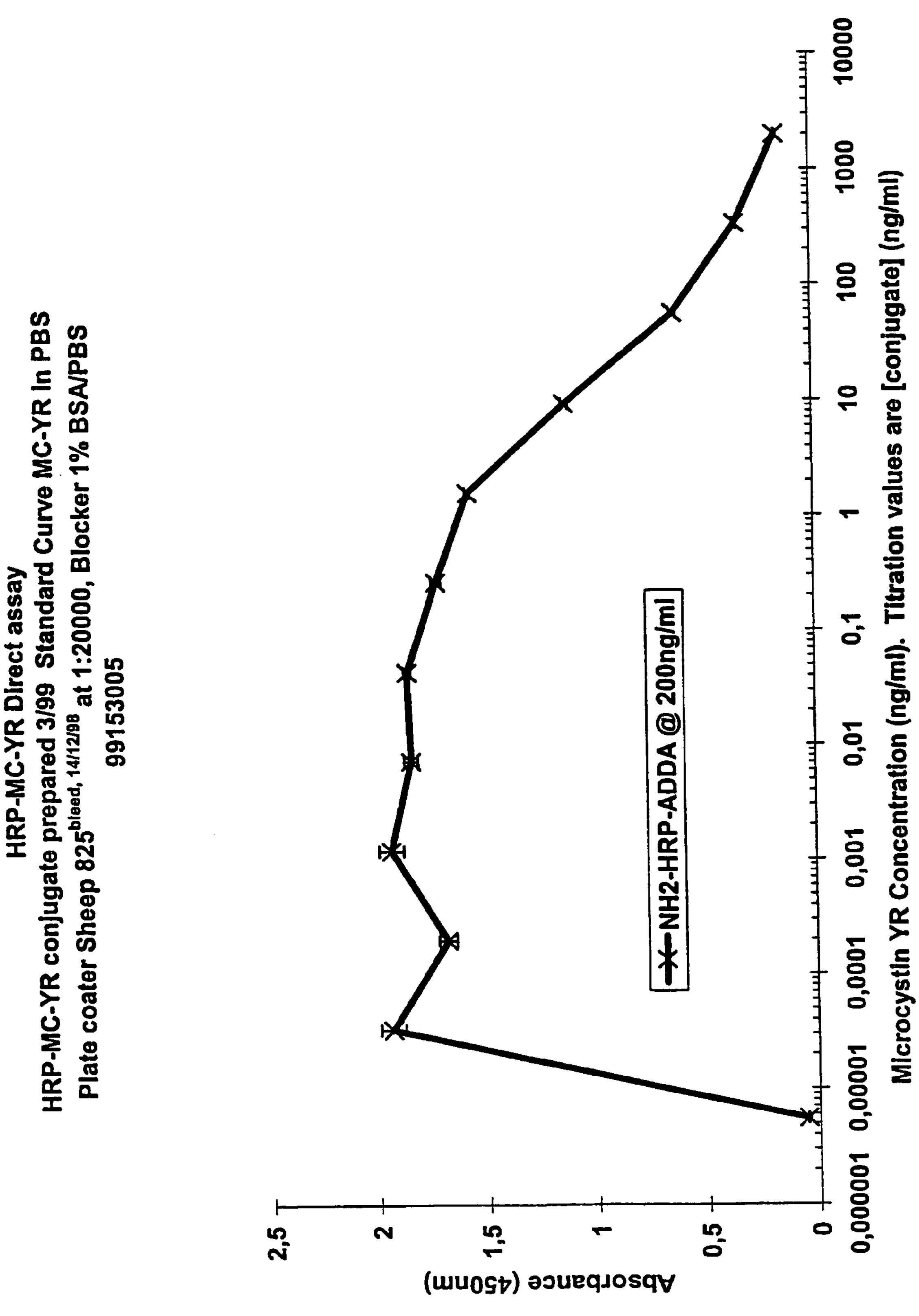
FIG. 6 is a diagram showing the direct ELISA method and its sensitivity for detection of MC-YR. The anti-ADDA antibody (ADDA-825-$^{bleed,14/12/98}$) was raised in sheep and directed against ADDA-HG coupled to ovalbumin.

Results of the above-described test are illustrated in FIG. 6.

Indirect ELISA using monoclonal antibody #3G10B 10 (assay 9910n001)

ELISA plates (NUNC MaxiSorp 1 #439454, Denmark) were coated with OVAADDA-HG conjugate in 0.05 M sodium bicarbonate buffer pH 9.6 (50 μl, 2.5 μg/ml) overnight at 20° C. After a wash with PBS, additional binding sites were blocked by incubation with BSA (1/% w/v, 300 μl, 1 h, 20–25° C.). Plates were washed two times with PBS and used immediately or stored at 4° C. for up to 7 days. In the assay, sample or standard (50 μl) was added to the wells together with monoclonal antibody (50 μl) at the appropriate dilution (e.g. #3G10B10 at 1/750). After incubation at 20–25° C. for 2 h, wells were washed twice with PBS+0.05%

Tween® 20 (PBST) and twice with PBS. After incubation at 20–25° C. for 2 h, wells were washed twice with PBS+0.05% Tween™20 (PBST) and twice with PBS. Secondary antibody, horse radish peroxitase conjugated anti-species antibody, e.g. Silenus DAH anti-mouse-HRP (100 μl, 1/2000), was then added to the wells and incubated for 2 h. TMB substrate solution, prepared by adding 110 μl TMB stock (10 mg/ml in DMSO) to 11 ml of sodium acetate buffer (0.1 M, pH 5.5) containing 0.005% $H_2O_2$, was then added and incubated for 15 minutes. The reaction was stopped by addition of $H_2SO_4$ (50 μl, 2 M), and the absorbance at 450 nm was determined with a microplate spectrophotometer. Standards were prepared for ELISA by dilution in the methanol in PBS to a maximum methanol concentration of 10% (v/v). All samples were analysed at least in duplicate and over a range of dilutions.

Figure 7:
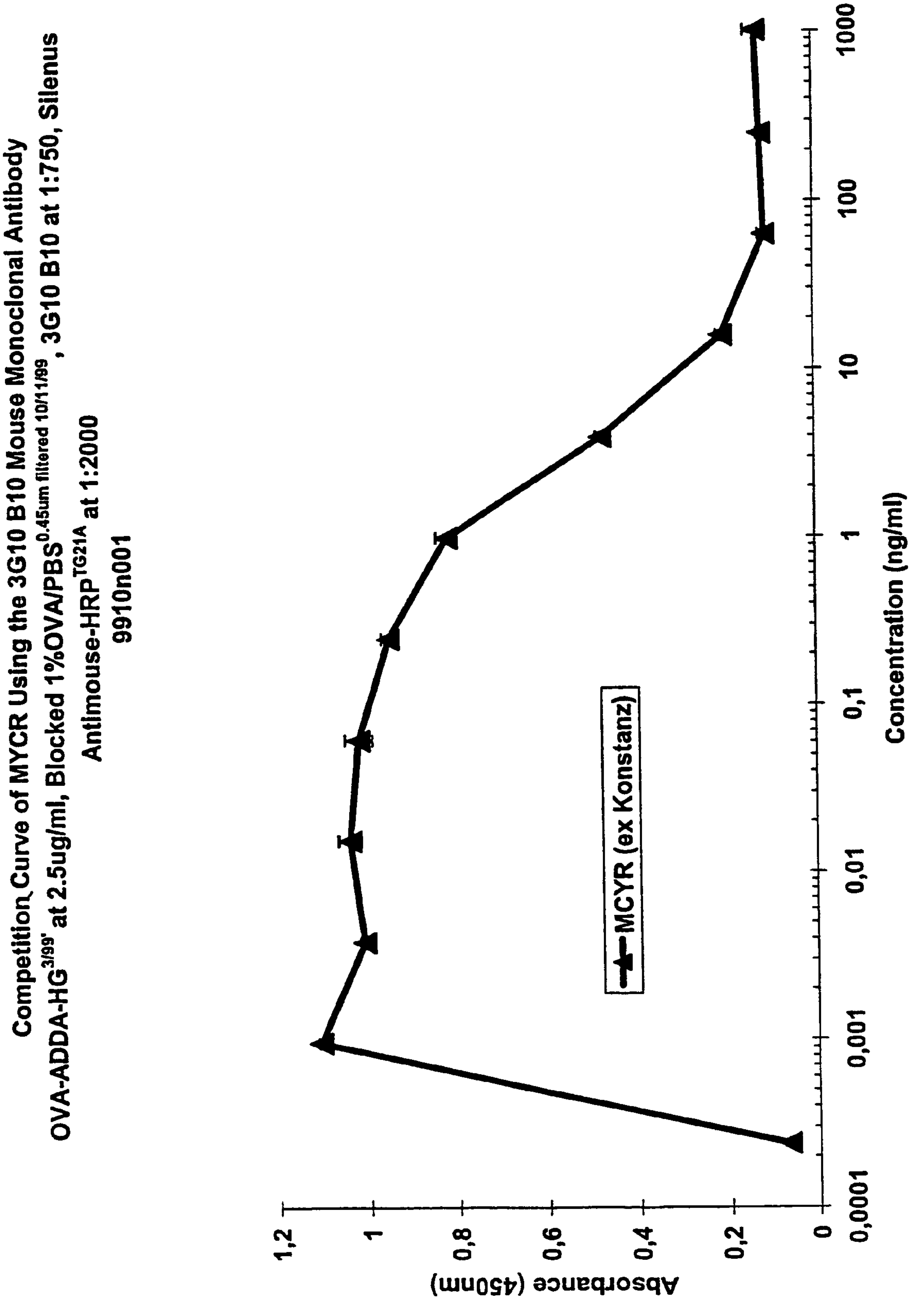
FIG. 7 is a diagram showing the indirect ELISA method using a monoclonal antibody and ist sensitivity for detection of MC-YR. The anti-ADDA antibody (ADDA-3G10B10) was raised in mice and directed against ADDA-HG coupled to ovalbumin.

Results of the above-described test are illustrated in FIG. 7.

ELISA method using antibody #3G10B10 in detail

The principle of the indirect competitive microcystin ELISA (MC-ELISA) employed is shown in FIG. 4. This method comprises the following steps:

1. Prepare antigen (OVA-ADDA-HG3199) in bicarbonate buffer, pH 9.6 at 2.5 μml (5 ml/plate).
2. Coat antigen onto microtitre plate at 50 μl/well, tap to mix and cover, incubate overnight at room temperature (RT, 22° C.).
3. Wash two times in PBS, aspirate.
4. Block plate with 1% BSA—(300 μl for 1 hour at RT (22° C.)).
5. Wash two times in PBS, aspirate and use immediately or add 2–300 μl PBS for storage. The plates can be stored at this stage in PBS (at 4° C.) for up to 7 days.
6. Add 50 μl sample, or standard, in PBS; and 50 μl of antibody #3G10 B10 at 1/750 dilution in BSA-blocker and incubate for 2 hours at RT (22° C.). Standard curve: Primary 1000 ng/ml, then nine serial 1:4 dilutions (1+3) in PBS.
7. Wash two times in PBS/Tween, two times in PBS.
8. Add 100 μl of secondary antibody conjugate diluted in OVA (Horseradish peroxidase-conjugated rabbit-anti-mouse IgG (Silenus DAH) at a final dilution of 1/2000 and incubate for 2 hours at RT (22 ° C.).
9. Wash two times in PBST, two times in PBS, aspirate.
10. Turn on plate reader—needs a 15 minute warm up before reading at step 13.
11. Add 100 μl of substrate. Incubate for 15 minutes at RT (22° C.) until colour develops.
12. Add 50 μl stop solution (2M $H_2SO_4$).
13. Read absorbance at 450 nm. Note that the absorbance at 655 nm can be measured prior to adding the stop solution if required.

PreDaration of Buffers:

Bicarbonate Coating Buffer

Dissolve 0.85 g $Na_2CO_3$, (or 2.15 g $Na_2CO_3$⁻2 $H_2O$) and 1.47 g $NaHCO_3$ in 500 ml distilled water, adjust pH to 9.6 (gives 0.05 M bicarbonate).

Phosphate Buffered Saline (PBS)

To prepare 10 times stock solution:
$NaH_2PO_4$⁻2 $H_2O$ 2.897 g (or $NaH_2PO_4$ anhydrous 2.06 g)
$Na_2HPO_4$ anhydrous 11.938 g
NaCl 87.660 g Weigh phosphates, add water to 800 ml, adjust pH to 7.4, then add salt.

Add water to 1 l and check pH (must be 7.2 to 7.6).

Dilute 1/10 for use: gives 0.01 M wrt phosphate and 0.15M NaCl.

Ref.: Mishell et al. (1980)

PBS/Tween

Suspend Tween-20 at 0.05% in PBS (0.5 ml/l);

Use for the washing steps desribed above.

OVA-Blocking Buffer

Dissolve OVA (Sigma A-5503) in PBS at 1% (2 g/200 ml).

Use for blocking plates, and as diluent for Ab and Ab".

Secondary Antibody

Also referred to herein as Ab", HRP-conjugate, and Second Ab. The dilution depends on the batch used, but approximate dilutions are as follows:

ICN HRP-Conjugated Rabbit-Anti-SHEEP-IgG #55814

Use at a working dilution of 1/3000. Stock solution is stored at 1/10 in PBS thiomersal (0.02%).

TMB Substrate

Prepare stocks of:

1) Sodium acetate buffer 0.1M, pH 5.5 (1.315 g/200 ml) (check for precipitate before use).

2) TMB (3,3',5,5'-tetramethylbenzidine) at 10 mg/ml DMSO; [store in the dark at RT (22° C.)].

Immediately before use:

Dissolve 110 μl TMB solution (2) in 11 ml sodium acetate buffer (1), and, add 165 $H_2O_2$ (prepared freshly by diluting 38 μl 30% $H_2O_2$ (commercial strength) into 2.5 ml distilled $H_2O$).

ELISA Plates 96-well-plates were from NUNC (Maxisorp 1 plates, catalogue #439454).

Characterization of polyclonal anti-ADDA-antibody developed in sheep

The optimal concentrations of assay reagents were determined empirically by chequerboard titrations. Assay standard curves were calculated using Microsoft Excel. Cutoff values of 20 to 80% of maximum absorbance were used in order to determine the working range. Cross-reactivity of the assay was determined against congeners of MC-LR, -RR, -YR, -LW, -LF, desmethyl-MC-LR, desmethyl-MC-RR and nodularin and calculated from the concentration of analogue giving 50% inhibition ($l_{50}$) of binding to the protein-ADDA solid phase, expressed relative to the $l_{50}$ for free microcystin-LR. The calculation of the cross-reactivity demonstrates that for sample concentrations ranging between 0.01 and 1 ng/ml the actual toxin concentrations are underestimated in the worst case by 5%. As of a sample concentration ranging betwee 1 ng/ml and 1 μg/l, most congeners tested are detected with equal sensitivity, i.e. 100% cross-reactivity (cf. FIG. 5), while the concentrations of MC-RR and nodularin are slightly overestimated (<5%). This demonstrates that microcystin and nodularin congeners can be detected reliably over a concentration range which is tenfold lower than the safe limit proposed by the WHO.

REFERENCES

Beasley, V. R., Cook, W. O., Dahlem, A. M., Hooser, S. B., Lovell, R. A. and Valentine, W. M. (1989) Algae intoxication in livestock and waterfowl. *Veterinary Clinical North American* (*Food Anim. Pract.*), 5, 345–361.

Billings, W. H. (1981) Water-associated human illness in Northeast Pennsylvania and its suspected association with blue-green algae blooms. In W. W. Carmichael (eds.), *The Water Environment— Algal Toxins and Health.* Plenum Press, New York, pp. 243–255.

Botes, D. P., Kruger, H. and Viljoen, C. C. (1982a) Isolation and characterization of four toxins from the blue-green alga Microcystis aeruginosa. *Toxicon,* 20, 945–954.

Botes, D. P., Viljoen, C. C., Kruger, H., Wessels, P. L. and Williams, D. H. (1982b) Configuration assignments of the amino acid residues and the presence N-methyldehydroalanine in toxins from the blue-green alga, Microcystis aeruginosa. *Toxicon,* 20, 1037–1042.

Botes, D. P., Tuinman, A. A., Wessels, P. L., Viljoen, C. C., Kruger, H., Williams, D. H., Santikarn, S., Smith, R. J. and Hammond, S. J. (1984) The structure of cyanoginosin-LA, a cyclic heptapeptide toxin from the cyanobacterium Microcystis aeruginosa. *Journal of Chemical Society, Perkin Transactions,* 1, 2311–2318.

Botes, D. P., Wessels, P. L., Kruger, H., Runnegar, M. T. C., Santikam, S., Smith, R. J., Barna, J. C. J. and Williams, D. H. (1985) Structural studies on cyanoginosins-LR, -YR, -YA, and -YM, peptide toxins from Microcystis aeruginosa. *J. Chem. Soc. Perkin Trans.,* 1, 2747–2748.

Carmichael, W. W., Mahmood, N. A. and Hyde, E. G. (1990) Natural toxins from cyanobacteria. In S. Hall and G. Strichartz (eds.), *Marine Toxins, Origin, Structure, and Molecular Pharmacology*. ACS, American Chemical Society, Washington, D.C., pp. 87–106.

Carmichael, W. W. (1994) The toxins of cyanobacteria. *Scientific American,* 270, 64–72.

Cousins, I. T., Bealing, D. J., James, H. A. and Sutton, A. (1996) Biodegradation of microcystin-LR by indigenous mixed bacterial populations. *Water Research,* 30, 481–485.

Eriksson, J. E., Toivola, D., Meriluoto, J. A. O., Karaki, H., Han, Y. -G. and Hartshorne, D. (1990) Hepatocyte deformation induced by cyanobacterial toxins reflects inhibition of protein phosphatases. *Biochemical and Biophysical Research Communications,* 173,1347–1353.

Falconer, I. R., Jackson, A. R. B., Langley, J. and Runnegar, M. T. C. (1981) Liver pathology in mice in poisoning by the blue-green alga Microcystis aeruginosa. *Australian Journal of Biological Sciences,* 34, 179–187.

Falconer, I. R., Beresford, A. M. and Runnegar, M. T. C. (1983) Evidence of liver damage by toxin from a bloom of the blue-green alga, Microcystis aeruginosa. *Medical Journal of Australia,* 1, 511–514.

Falconer, I. R. (1991) Tumor promotion and liver injury caused by oral consumption of cyanobacteria. *Environmental Toxicology and Water Quality,* 6, 177–184.

Falconer, I. R., Choice, A. and Hosja, W. (1992) Toxicity of edible mussels (Mytilus edulis) growing naturally in an estuary during a water bloom of the blue-green alga Nodularia spumigena. *Environmental Toxicology and Water Quality,* 7, 119–123.

Francis, G. (1878) Poisonous Australian lake. *Nature,* 18, 11–12.

Honkanen, R. E., Zwiller, J., Moore, R. E., Daily, S. L., Khatra, B. S., Dukelow, M. and Boynton, A. L. (1990) Characterization of microcystin-LR, a potent inhibitor of type 1 and type 2A protein phosphatases. *Joumal of Biological Chemistry,* 265, 19401–4.

Hooser, S. B., Kuhlenschmidt, M. S., Beasley, V. R., Carmichael, W. W. and Haschek, W. M. (1990) Mirocystin-LR uptake and localization in rat liver and hepatocyte suspensions (abstract). *Toxicologist,* 10, 294.

Humphrey, J. M., Aggen, J. and Chamberlin, A. R. *J. Am. Chem. Soc.* 1996, 118, 11759–11770. "Synthesis of the Serine-threonine Phosphatase Inhibitor Microcystin LA."

Jackson, A. R. B., McInnes, A., Falconer, I. R. and Runnegar, M. T. C. (1984) Clinical and pathological changes in sheep experimentally poisoned by the blue-green alga Microcystis aeruginosa. *Veterinary Pathology,* 21, 102–113.

James, H. A., James, C. P. and Hart, J. (1994) The analysis of microcystin-LR in water: Application in water treatment studies. In G. A. Codd, T. M. Jefferies, C. W. Keevil and E. Potter (eds.), *Detection methods for cyanobacterial toxins.* The Royal Society of Chemistry, Cambridge, pp. 51–58.

Keleti, G., Sykora, J. L., Maiolie, L. A., Doerfler, D. L. and Campbell, I. M. (1981) Isolation and characterization of endotoxin from cyanobacteria (blue-green algae). In W. W. Carnichael (eds.), *The Water Environment, Algal Toxins and Health*. Plenum Press, New York, pp. 447–464.

Kenefick, S. L., Hrudey, S. E., Peterson, H. G. and Prepas, E. E. (1993) Toxin release from Microcystis aeruginosa after chemical treatment. *Water Science and Technology,* 27, 433–440.

Kondo, F., Ikai, Y., Oka, H., Okumura, M., Ishikawa, N., Harada, K.-I., Matsuura, K., Murata, H. and Suzuki, M. (1992) Formation, characterization, and toxicity of the glutathione and cysteine conjugates of toxic heptapeptide microcystins. *Chemical Research and Toxicology.* 5, 591–596.

Lawton, L. A., Edwards, C. and Codd, G. A. (1994) Extraction and high-performance liquid-chromatographic method for the determination of microcystins in raw and treated waters. *Analyst,* 119, 1525–1530.

MacKintosh, C., Beattie, K. A., Klumpp, S., Cohen, P. and Codd, G.A. (1990) Cyanobacterial microcystin-LR is a potent and specific inhibitor of protein phosphatases 1 and 2A from both mammals and higher plants. *FEBS Letters,* 264, 187–92.

MacKintosh, R. W., Dalby, K. N., Campbell, D. G., Cohen, P. T., Cohen, P. and MacKintosh, C. (1995) The cyanobacterial toxin microcystin binds covalently to cysteine-273 on protein phosphatase 1. *FEBS Letters,* 371, 236–240.

Mahmood, N. A., Carmichael, W. W. and Pfahler, D. (1988) Anticholinesterase poisonings in dogs from a cyanobacterial (blue-green algae) bloom dominated by Anabaena flos-aquae. *American Journal of Veterinary Research,* 49, 500–503.

Mishell, B. B and Shiigi, S. M. (1980) Selected Methods in Cellular Immunology. Freeman & Co, San Francisco, page 458.

Matsushima, R., Yoshizawa, S., Watanabe, M. F., Harada, K., Furusawa, M., Carmichael, W. W. and Fujiki, H. (1990) In vitro and in vivo effects of protein phosphatase inhibitors, microcystins and nodularin, on mouse skin and fibroblasts. *Biochemical and Biophysical Research Communications,* 171, 867–74.

Nishiwaki-Matsushima, R., Ohta, T., Nishiwaki, S., Suganuma, M., Kohyama, K., Ishikawa, T., Carmichael, W. W. and Fujiki, H. (1992) Liver tumor promotion by the cyanobacterial cyclic peptide toxin microcystin-LR. *Journal of Cancer Research and Clinical Oncology,* 118, 420–424.

Rinehart, K. L., Harada, K.-I., Namikoshi, M., Chen, C., Harvis, C. A., Munro, M. H. G., Blunt, J. W., Mulligan, P. E., Beasley, B. R., Dahlem, A. M. and Carmichael, W. W. (1988) Nodularin, Microcystin, and the Configuration of ADDA. *Journal of the American Chemical Society,* 110, 8557–8558.

Runnegar, M. T. C., Gerdes, R. G. and Falconer, I. R. (1991) The uptake of the cyanobacterial hepatotoxin microcystin by isolated rat hepatocytes. *Toxicon,* 29, 43–51.

Runnegar, M., Berndt, N., Kong, S., Lee, E. Y. C. and Zhang, L. (1996) In vivo and in vitro binding of microcystin to protein phosphatases 1 and 2A (abstract). *Toxicologist,* 30, 330.

Sherlock, l. R., Furey, A., James, K. J., Caudwell, F. B. and MacKintosh, C. (1998) New methods for the detection and identification of cyanobacterial toxins and their application to Irish freshwater. In: Reguera, B., Blanco, J., Femandez, M. L., Wyatt, T. Harmful Algae, VIII International Conference, Vigo, Spain, 529–532.

Sivonen, K., Namikoshi, M., Evans, W. R., Carmichael, W. W., Sun, F., Rouhiainen, L., Luukkainen, R. and Rinehart, K. L. (1992a) Isolation and characterization of a variety of microcystins from seven strains of the cyanobacterial genus *Anabaena. Applied Environmental Microbiology,* 58, 2495–500.

Sivonen, K., Namikoshi, M., Evans, W. R., Gromov, B. V., Carmichael, W. W. and Rinehart, K. L. (1992b) Isolation and structures of five microcystins from a Russian Microcystis aeruginosa strain CALU 972. *Toxicon,* 30, 1481–5.

Sivonen, K., Skulberg, O. M., Namikoshi, M., Evans, W. R., Carmichael, W. W. and Rinehart, K. L. (1992c) Two methyl ester derivatives of microcystins, cyclic heptapeptide hepatotoxins, isolated from Anabaena flos-aquae strain CYA 83/1. *Toxicon,* 30, 1465–71.

Skulberg, O. M., Codd, G. A. and Carmichael, W. W. (1984) Toxic blue-green algal blooms in Europe: A growing problem. *Ambio,* 13, 244–247.

Tencalla, F. G., Dietrich, D. R. and Schlatter, C. (1994) Toxicity of Microcystis aeruginosa peptide toxin to yearling rainbow trout (Oncorhynchus mykiss). *Aquatic Toxicology,* 30, 215–224.

Tencalla, F. (1995) Toxicity of cyanobacterial peptide toxins to fish. Ph.D. Thesis, ETH Zürich.

Theiss, W. C., Carmichael, W. W., Wyman, J. and Bruner, R. (1988) Blood pressure and hepatocallular effects of the cyclic heptapeptide toxin produced by the freshwater cyanobacterium (blue-green alga) Microcystis aeruginosa strain PCC-7820. *Toxicon,* 26, 603–613.

Tisdale, E. S. (1931) Epidemic of intestinal disorders in Charleston, W. VA., occurring simultaneously with unprecedented water supply conditions. *American Journal of Public Health,* 21, 198–200.

Tsuji, K., Naito, S., Kondo, F., Ishikawa, N., Watanabe, M. F., Suzuki, M. and Harada, K.-I. (1994) Stability of microcystins from cyanobacteria: Effect of light on decompostition and isomerization. *Environmental Science and Technology,* 28, 173–177.

Watanabe, M. M., Kaya, K. and Takamura, N. (1992a) Fate of the toxic cyclic heptapeptides, the microcystins, from blooms of Microcystis (cyanobacteria) in a hypertrophic lake. *Journal of Phycology,* 28, 761–767.

Watanabe, M. F., Tsuji, K., Watanabe, Y., Harada, K.-I. and Suzuki, M. (1992b) Release of heptapeptide toxin (microcystin) during the decomposition process of Microcystis aeruginosa. *Natural Toxins,* 1, 48–53.

Wicks, R. J. and Thiel, P. G. (1990) Environmental factors affecting the production of peptide toxins in floating scums of the cyanobacterium Microcystis aeruginosa in a hypertrophic African reservoir. *Environmental Science and Technology,* 24, 1413–1418.

Yoshizawa, S., Matsushima, R., Watanabe, M. F., Harada, K.-I., Ichihara, A., Carmichael, W. W. and Fujiki, H. (1990) Inhibition of protein phosphatases by microcystin and nodularin associated with hepatotoxicity. *Journal of Cancer Research and Clinical Oncology,* 116, 609–614.

What is claimed is:

1. A compound comprising one or more polypeptides providing a binding site of a monoclonal, polyclonal or recombinant antibody or a functionally active derivative or part thereof, wherein said compound is prepared using the group of formula (I) as a hapten, and said compound is capable of specifically binding to a compound having a structure of formula (I) represented as (I)

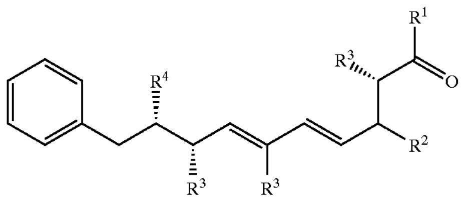

wherein group $R^1$ represents a halogen atom, $-OSO_3$, -OR' or $-NR'_2$ and group $R^2$ represents hydrogen, $(C_1–C_4)$alkyl, $(C_1–C_4)$alkoxy, $(C_1–C_4)$acyl, $(C_1–C_4)$acylamino, $(C_1–C_4)$ carboxyaminoacyl, glutamidyl, or 2-aminopropionamidyl, and wherein the groups $R^3$ which may be the same or different are each independently selected from the group consisting of hydrogen and $(C_1–C_4)$alkyl, group $R^4$ represents $(C_1–C_4)$ alkoxy, the phenyl group may be substituted or unsubstituted, and further wherein the groups R' represent hydrogen, substituted or unsubstituted $(C_1–C_4)$alkyl or $(C_1–C_4)$acyl.

2. The compound according to claim 1, wherein the groups $R^3$ each represent methyl and group $R^4$ represents methoxy.

3. A compound comprising one or more polypeptides providing a binding site of a monoclonal, polyclonal or recombinant antibody or a functionally active derivative or part thereof, wherein said compound is prepared using the group of formula (I) as a hapten, and said compound is capable of specifically binding to a compound having a structure of formula (I) represented as

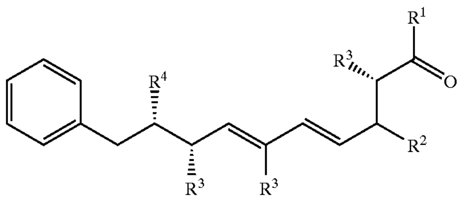

(I)

wherein group $R^1$ represents acylamino and group $R^2$ represents $(C_1–C_4)$acyl; or group $R^1$ represents glycyl or D-alanyl and group $R^2$ represents acetyl; or group $R^1$ represents $-NH_2$ and group $R^2$ represents glutamidyl or 2-aminopropionamidyl, and wherein the groups $R^3$ which may be the same or different are each independently selected from the group consisting of hydrogen and $(C_1–C_4)$ alkyl, group $R^4$ represents $(C_1-C_4)$alkoxy, the phenyl group may be substituted or unsubstituted, and further wherein the groups $R^1$ represent hydrogen, substituted or unsubstituted $(C_1–C_4)$alkyl or $(C_1–C_4)$ acyl.

4. The compound according to claim 3, wherein the groups $R^3$ each represent methyl and group $R^4$ represents methoxy.

5. The compound according to claim 1 or claim 3 which is a polyclonal, monoclonal or recombinant antibody or a functionally active derivative or fragment thereof.

6. A method for preparation of the compound according to claim 1 or claim 3, said method comprising the steps of:

(a) providing a compound containing a group represented by formula (I) as defined in claim 1 or claim 3;

(b) coupling the compound of step (a) to an immunogenic carrier to form a conjugate;

(c) immunizing an animal with the conjugate obtained in step (b); and (d) isolating the animal's blood, blood serum and/or spleenocytes.

7. The method according to claim 6, wherein the immunogenic carrier is a polymeric substance.

8. The method according to claim 7, wherein the polymeric substance is selected from the group consisting of polyethyleneglycol, polypeptides, proteins, polysaccharides and plastic supports.

9. The method according to claim 8, wherein the substance is a protein and said protein is selected from bovine serum albumin, ovalbumin, cationised bovine serum albumin or horseradish peroxidase.

10. A diagnostic kit containing the compound according to claim 1 or claim 3.

11. An affinity matrix containing the compound according to claim 1 or claim 3 coupled to a polymeric resin.

12. A method for detecting a compound containing a group represented by formula (I) as defined in claim 1 or claim 3, said method comprising the steps of:

(a) providing a compound according to claim 1 or claim 3;

(b) mixing a second compound suspected of containing a group represented by formula (I) as defined in claim 1 or claim 3 to form a mixture; and (c) performing an assay that detects binding of the compound according to claim 1 or claim to the second compound.

13. A method for concentrating a compound containing a group represented by formula (I) as defined in claim 1 or claim 3 from a fluid or for substantially decreasing the amount of a compound containing the group represented by formula (I) in a fluid comprising the steps of:

(a) preparing the compound according to claim 1 or claim 3, (b) coupling the compound obtained in step (a) to a polymeric matrix, and (c) contacting the fluid with the polymeric matrix obtained in step (b).

14. The method according to claim 13, wherein the fluid is hemodialysis water, drinking water or water derived from rivers, lakes or oceans.

* * * * *

UNITED STATES PATENT AND TRADEMARK OFFICE
CERTIFICATE OF CORRECTION

PATENT NO. : 6,967,240 B1
APPLICATION NO. : 10/070302
DATED : November 22, 2005
INVENTOR(S) : Daniel R. Dietrich et al.

It is certified that error appears in the above-identified patent and that said Letters Patent is hereby corrected as shown below:

Inventors (75), line 5, “San Francisco, CA (US)” should read --Burlingame, CA (US)--;

Inventors (75), line 7, “Oslo (NO)” should read --Hamilton (NZ)--;

Abstract (57), line 6, “affinty” should read affinity--;

Column 2, line 16, “halflifetimes” should read --half-lifetimes--;

Column 5, line 31, “trimethyl-lphenyldeca-4,6-dienic acid” should read --trimethyl-10-phenyldeca-4,6-dienic acid--;

Column 5, line 40, “9 of dry” should read --g of dry--;

Column 7, line 44, “ant-ADDA” should read --anti-ADDA--;

Column 8, line 27, within the blocked diagram, “N-Boc-Adda-OMe” should read --N-Ac-Adda-OMe--;

Column 9, line 35, “% 0.99” should read --‰ 0.99--;

Column 9, line 41, “$C_{22H32}NO_4$” should read --$C_{22}H_{32}NO_4$--;

Column 10, line 38, within blocked diagram, “$CO_2Me$” should read --$CO_2H$--;

Column 10, line 50, “0.01 1 mmol)” should read --(0.011 mmol)--;

Column 10, line 51, “1.7r) ml” should read --1.75 ml--;

Column 11, line 18, “(100 $\mu$I)” should read --(100 $\mu$l)--;

Column 11 and 12, bottom of page, replace the formula that spans both columns with the following:

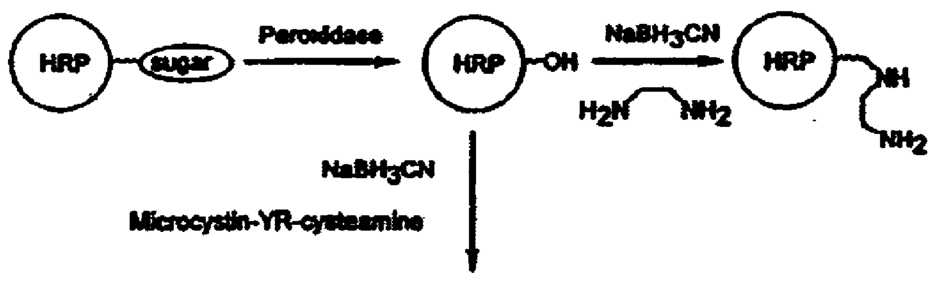

UNITED STATES PATENT AND TRADEMARK OFFICE

CERTIFICATE OF CORRECTION

PATENT NO. : 6,967,240 B1 
APPLICATION NO. : 10/070302
DATED : November 22, 2005
INVENTOR(S) : Daniel R. Dietrich et al.

It is certified that error appears in the above-identified patent and that said Letters Patent is hereby corrected as shown below:

Column 16, line 58, “ESI-MS mlz” should read --ESI-MS m/z--;

Column 16, line 64, “cBSAADDA-and” should read --cBSA-ADDA-and--;

Column 18, line 9, “polvclonal” should read --polyclonal--;

Column 18, line 64, “#3G10B 10” should read --#3G10B10--.

Column 19, line 36, “2.5 $\mu$ml” should read --2.5 $\mu$g/ml--;

Column 20, line 1, “PreDaration” should read --Preparation--;

Column 20, line 43, “165 $H_2O_2$” should read --165 $\mu$l $H_2O_2$--; and

Column 26, claim 12, line 24, “claim to” should read --claim 3 to--.

Signed and Sealed this

Seventeenth Day of October, 2006

JON W. DUDAS
*Director of the United States Patent and Trademark Office*